United States Patent
Deligny et al.

(10) Patent No.: US 10,654,861 B2
(45) Date of Patent: May 19, 2020

(54) FUSED PENTACYCLIC IMIDAZOLE DERIVATIVES AS MODULATORS OF TNF ACTIVITY

(71) Applicants: UCB Biopharma SRL, Brussels (BE); Sanofi, Paris (FR)

(72) Inventors: Michael Louis Robert Deligny, Brussels (BE); Jag Paul Heer, Slough (GB); Jean Keyaerts, Brussels (BE); Luce Elsa Lepissier, Montreal (CA); Martin Alexander Lowe, Slough Berkshire (GB)

(73) Assignee: UCB Biopharma SRL, Brussels (BE)

( * ) Notice: Subject to any disclaimer, the term of this patent is extended or adjusted under 35 U.S.C. 154(b) by 0 days.

(21) Appl. No.: 16/086,408

(22) PCT Filed: Mar. 31, 2017

(86) PCT No.: PCT/EP2017/057767
§ 371 (c)(1),
(2) Date: Sep. 19, 2018

(87) PCT Pub. No.: WO2017/167994
PCT Pub. Date: Oct. 5, 2017

(65) Prior Publication Data
US 2019/0100525 A1 Apr. 4, 2019

(30) Foreign Application Priority Data
Apr. 1, 2016 (EP) ..................... 16163579

(51) Int. Cl.
*C07D 487/18* (2006.01)
*C07D 487/04* (2006.01)

(52) U.S. Cl.
CPC ......... *C07D 487/18* (2013.01); *C07D 487/04* (2013.01)

(58) Field of Classification Search
CPC ............................ C07D 487/18; C07D 487/04
USPC ........................................ 514/256
See application file for complete search history.

(56) References Cited

U.S. PATENT DOCUMENTS

2015/0152065 A1   6/2015   Brookings et al.

FOREIGN PATENT DOCUMENTS

| WO | WO 2004/087720 | 10/2004 |
|----|----------------|---------|
| WO | WO 2009/156091 | 12/2009 |
| WO | WO 2012/135082 | 10/2012 |
| WO | WO 2012/177707 | 12/2012 |
| WO | WO 2013/186229 | 12/2013 |
| WO | WO 2014/009295 | 1/2014 |
| WO | WO 2014/009296 | 1/2014 |
| WO | WO 2015/086525 | 6/2015 |
| WO | WO 2015/086526 | 6/2015 |
| WO | WO 2016/050975 | 4/2016 |

OTHER PUBLICATIONS

Tansey & Szymkowski, Drug Discovery Today, 2009, 14, 1082-1088.
Carneiro et al., J. Secual Medicine, 2010, 7, 3823-3834.
Wu et al., JAMA, 2013, 309, 2043-2044.
Hauwemeiren et al., J. Clin, Invest., 2013, 123, 2590-2603.
Hilpert et al., Journal of medicinal Chemistry, 2013, 56(10), 3980-3995.
Armstrong et al., J. Org. Chem., 2013, 78, 10534.
Nagib & McMillan, Nature, 2011, 480, 224.
Bentley et al., Organic Process Research & Development, 2002, 6(2) 109-112.
Nam et al., Bio-org. Med. Chem., 2004, 12, 6255.
Lacko et al., Current Medicinal Chemistry, 2012, 19, 4699.

*Primary Examiner* — Kahsay Habte
(74) *Attorney, Agent, or Firm* — McDonnell Boehnen Hulbert & Berghoff LLP

(57) ABSTRACT

A series of substituted fused pentacyclic benzimidazole derivatives, and analogues thereof, being potent modulators of human TNFα activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

9 Claims, No Drawings

FUSED PENTACYCLIC IMIDAZOLE DERIVATIVES AS MODULATORS OF TNF ACTIVITY

This application is a US national stage application under 35 U.S.C. § 371 of International Application No. PCT/EP2017/057767, filed Mar. 31, 2017, which claims priority to European Application No. 16163579.2, filed Apr. 1, 2016.

The present invention relates to a class of fused pentacyclic imidazole derivatives, and to their use in therapy. More particularly, this invention is concerned with pharmacologically active substituted fused pentacyclic benzimidazole derivatives and analogues thereof. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Cameiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

WO 2013/186229, WO 2014/009295 and WO 2014/009296 relate to fused bicyclic imidazole derivatives which are modulators of the signalling of TNFα.

WO 2015/086525 and WO 2015/086526 relate to fused tricyclic imidazole derivatives which are modulators of the signalling of TNFα.

Co-pending international patent application PCT/EP2015/072868 (published on 7 Apr. 2016 as WO 2016/050975) relates to fused pentacyclic imidazole derivatives which are modulators of the signalling of TNFα.

None of the prior art available to date, however, discloses or suggests the precise structural class of fused pentacyclic imidazole derivatives as provided by the present invention.

The present invention provides a compound of formula (I) or an N-oxide thereof, or a pharmaceutically acceptable salt thereof:

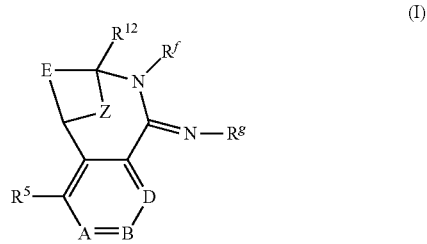

wherein
A represents N or C—$R^6$;
B represents N or C—$R^7$;
D represents N or C—$R^8$;
E represents a fused heteroaromatic ring system selected from the groups of formula (Ea), (Eb) and (Ec):

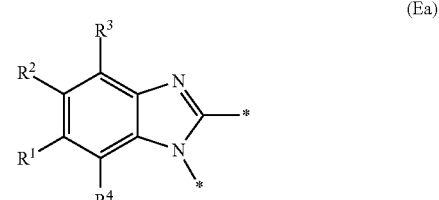

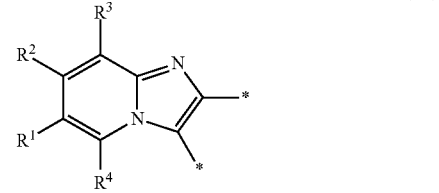

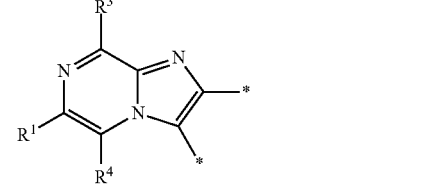

wherein the asterisks (*) represent the site of attachment of E to the remainder of the molecule;

$R^1$ represents hydrogen, halogen, cyano, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$COR^d$, —$CO_2R^d$, —$CONR^bR^c$, —$SO_2NR^bR^c$, or —$S(O)(N—R^b)R^c$; or $R^1$ represents $C_{1-6}$ alkyl, $C_{3-7}$ cycloalkyl, $C_{4-7}$ cycloalkenyl, aryl, aryl($C_{1-6}$)alkyl, $C_{3-7}$ heterocycloalkyl, $C_{3-7}$ heterocycloalkenyl, heteroaryl, heteroaryl($C_{1-6}$)alkyl, ($C_{3-7}$)heterocycloalkyl($C_{1-6}$)alkyl-aryl-, ($C_{3-7}$)heterocycloalkenyl-aryl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

$R^2$ represents hydrogen, halogen, cyano, nitro, hydroxy, trifluoromethyl, trifluoromethoxy or —$OR^a$; or $R^2$ represents $C_{1-6}$ alkyl or heteroaryl, either of which groups may be optionally substituted by one or more substituents;

$R^3$ and $R^4$ independently represent hydrogen, halogen or trifluoromethyl; or $C_{1-6}$ alkyl, which group may be optionally substituted by one or more substituents;

$R^5$ represents hydrogen, halogen, hydroxy, cyano, trifluoromethyl, difluoromethoxy, trifluoromethoxy, —$OR^a$ or $C_{1-6}$ alkylsulphonyl; or $R^5$ represents $C_{1-6}$ alkyl, which group may be optionally substituted by one or more substituents;

$R^6$, $R^7$ and $R^8$ independently represent hydrogen, halogen, trifluoromethyl, $C_{1-6}$ alkyl or $C_{1-6}$ alkoxy;

$R^{12}$ represents hydrogen or $C_{1-6}$ alkyl;

$R^a$ represents $C_{1-6}$ alkyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl and (dioxo)-thiazinan-4-yl, any of which groups may be optionally substituted by one or more substituents;

$R^d$ represents hydrogen; or $R^d$ represents $C_{1-6}$ alkyl, $C_{3-7}$ cycloalkyl, aryl, $C_{3-7}$ heterocycloalkyl or heteroaryl, any of which groups may be optionally substituted by one or more substituents;

$R^e$ represents $C_{1-6}$ alkyl, aryl or heteroaryl, any of which groups may be optionally substituted by one or more substituents; and $R^f$ and $R^g$ independently represent hydrogen or $C_{1-6}$ alkyl.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of TNFα function is indicated.

In another aspect, the present invention provides the use of a compound of formula (I) as defined above or an N-oxide thereof, or a pharmaceutically acceptable salt thereof, for the manufacture of a medicament for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one or two substituents.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds in accordance with the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Suitable alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[3.1.0]hexanyl, bicyclo[4.1.0]heptanyl and bicyclo[2.2.2]octanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, dioxanyl, tetrahydrothiopyranyl, piperidinyl, 1,2,3,4-tetrahydroquinolinyl, 1,2,3,4-tetrahydro-isoquinolinyl, piperazinyl, 1,2,3,4-tetrahydroquinoxalinyl, hexahydro-[1,2,5]thiadiazolo-[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,7-dioxa-9-azabicyclo-[3.3.1]nonanyl and 3,9-diazabicyclo[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom. Suitable spiroheterocycloalkyl groups include 5-azaspiro[2.3]hexanyl, 5-azaspiro[2.4]heptanyl, 2-azaspiro[3.3]heptanyl, 2-oxa-6-azaspiro[3.3]heptanyl, 2-oxa-6-azaspiro[3.4]-octanyl, 2-oxa-6-azaspiro[3,5]nonanyl, 7-oxa-2-azaspiro[3,5]nonanyl, 2-oxa-7-azaspiro-[3,5]nonanyl and 2,4,8-triazaspiro[4,5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]-pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C\!=\!O$)↔enol ($CH\!=\!CHOH$) tautomers or amide ($NHC\!=\!O$)↔hydroxy-imine ($N\!=\!COH$) tautomers. Formula (I) and the formulae depicted hereinafter are intended to represent all individual tautomers and all possible mixtures thereof, unless stated or shown otherwise.

As will be appreciated, 2-oxo-(1H)-pyridinyl is a tautomer of 2-hydroxypyridinyl; and 2-oxo-(1H)-pyrimidinyl is a tautomer of 2-hydroxypyrimidinyl.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}$C, $^{13}$C or $^{14}$C atom, preferably $^{12}$C.

A particular sub-class of compounds in accordance with the present invention is represented by formula (IA) or an N-oxide thereof, or a pharmaceutically acceptable salt thereof:

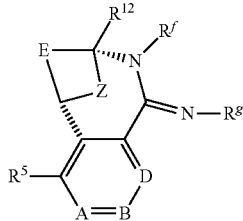

(IA)

wherein A, B, D, Z, E, $R^5$, $R^{12}$, $R^f$ and $R^g$ are as defined above.

In a first embodiment, A represents N. In a second embodiment, A represents C—$R^6$.

In a first embodiment, B represents N. In a second embodiment, B represents C—$R^7$.

In a first embodiment, D represents N. In a second embodiment, D represents C—$R^8$.

In a first embodiment, A, B and D all represent N. In a second embodiment, A and B both represent N, and D represents C—$R^8$. In a third embodiment, A and D both represent N, and B represents C—$R^7$. In a fourth embodiment, A represents N, B represents C—$R^7$, and D represents C—$R^8$. In a fifth embodiment, A represents C—$R^6$, and B and D both represent N. In a sixth embodiment, A represents C—$R^6$, B represents N, and D represents C—$R^8$. In a seventh embodiment, A represents C—$R^6$, B represents C—$R^7$, and D represents N. In an eighth embodiment, A represents C—$R^6$, B represents C—$R^7$, and D represents C—$R^8$.

Suitably, at least one of A, B and D is other than N.

Generally, E represents a fused heteroaromatic ring system of formula (Ea) or (Eb).

In a first embodiment, E represents a fused heteroaromatic ring system of formula (Ea).

In a second embodiment, E represents a fused heteroaromatic ring system of formula (Eb).

In a third embodiment, E represents a fused heteroaromatic ring system of formula (Ec).

Particular sub-classes of compounds in accordance with the present invention include the compounds of formula (IB), (IC) and (ID) and N-oxides thereof, and pharmaceutically acceptable salts thereof:

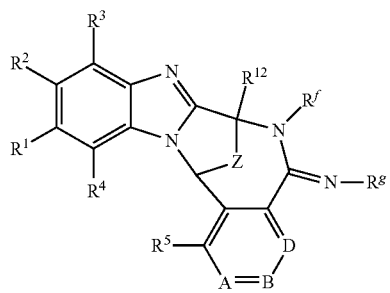

(IB)

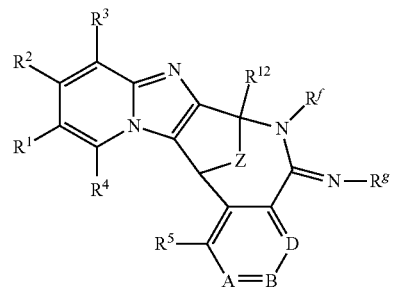

(IC)

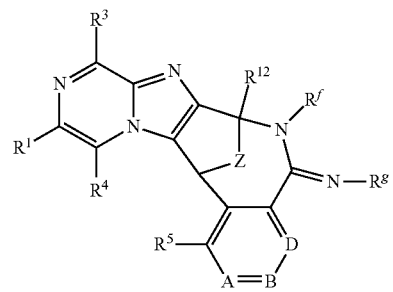

(ID)

wherein A, B, D, Z, $R^1$, $R^2$, $R^3$, $R^4$, $R^5$, $R^{12}$, $R^f$ and $R^g$ are as defined above.

Particular sub-classes of compounds in accordance with the present invention include the compounds of formula (IB) and (IC) as defined above.

A particular sub-class of compounds in accordance with the present invention is represented by formula (IB) as defined above.

Generally, $R^1$ represents hydrogen, halogen or cyano; or $R^1$ represents aryl, $C_{3-7}$ heterocycloalkyl, $C_{3-7}$ heterocycloalkenyl, heteroaryl, heteroaryl-aryl-, $(C_{3-7})$cycloalkyl-heteroaryl-, $(C_{4-9})$bicycloalkyl-heteroaryl-, $(C_{3-7})$heterocycloalkyl-heteroaryl-, $(C_{4-9})$-heterobicycloalkyl-heteroaryl- or $(C_{4-9})$spiroheterocycloalkyl-heteroaryl-, any of which groups may be optionally substituted by one or more substituents.

Typically, $R^1$ represents halogen; or $R^1$ represents $C_{3-7}$ heterocycloalkyl, heteroaryl, $(C_{3-7})$cycloalkyl-heteroaryl-, $(C_{3-7})$heterocycloalkyl-heteroaryl- or $(C_{4-9})$-heterobicycloalkyl-heteroaryl-, any of which groups may be optionally substituted by one or more substituents.

Suitably, $R^1$ represents halogen; or $R^1$ represents heteroaryl, which group may be optionally substituted by one or more substituents.

More suitably, $R^1$ represents heteroaryl, which group may be optionally substituted by one or more substituents.

In a first embodiment, $R^1$ represents hydrogen.

In a second embodiment, $R^1$ represents halogen. In one aspect of that embodiment, $R^1$ represents fluoro. In another aspect of that embodiment, $R^1$ represents chloro.

In a third embodiment, $R^1$ represents cyano.

In a fourth embodiment, $R^1$ represents optionally substituted aryl. In one aspect of that embodiment, $R^1$ represents optionally substituted phenyl.

In fifth embodiment, $R^1$ represents optionally substituted $C_{3-7}$ heterocycloalkyl. In one aspect of that embodiment, $R^1$ represents optionally substituted azetidinyl.

In a sixth embodiment, $R^1$ represents optionally substituted $(C_{3-7})$heterocycloalkenyl. In a first aspect of that embodiment, $R^1$ represents optionally substituted 1,2-dihydropyridinyl. In a second aspect of that embodiment, $R^1$ represents optionally substituted 1,2-dihydropyrimidinyl.

In a seventh embodiment, $R^1$ represents optionally substituted heteroaryl. In one aspect of that embodiment, $R^1$ represents optionally substituted pyridinyl. In another aspect of that embodiment, $R^1$ represents optionally substituted pyrimidinyl.

In an eighth embodiment, $R^1$ represents optionally substituted heteroaryl-aryl-. In one aspect of that embodiment, $R^1$ represents optionally substituted imidazolylphenyl-.

In a ninth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclopropylpyridinyl-. In a third aspect of that embodiment, $R^1$ represents optionally substituted cyclobutylpyridinyl-. In a fourth aspect of that embodiment, $R^1$ represents optionally substituted cyclopentylpyridinyl-. In a fifth aspect of that embodiment, $R^1$ represents optionally substituted cyclohexylpyridinyl-. In a sixth aspect of that embodiment, $R^1$ represents optionally substituted cyclopropylpyrimidinyl-. In a seventh aspect of that embodiment, $R^1$ represents optionally substituted cyclobutylpyrimidinyl-. In an eighth aspect of that embodiment, $R^1$ represents optionally substituted cyclopentylpyrimidinyl-. In a ninth aspect of that embodiment, $R^1$ represents optionally substituted cyclohexylpyrimidinyl-. In a tenth aspect of that embodiment, $R^1$ represents optionally substituted cyclohexylpyrazinyl-.

In a tenth embodiment, $R^1$ represents optionally substituted $(C_{4-9})$bicycloalkyl-heteroaryl-.

In an eleventh embodiment, $R^1$ represents optionally substituted $(C_3$-7$)$-heterocycloalkyl-heteroaryl-. In a first aspect of that embodiment, $R^1$ represents substituted azetidinylpyrazolyl-. In a second aspect of that embodiment, $R^1$ represents optionally substituted pyrrolidinylpyridinyl-. In a third aspect of that embodiment, $R^1$ represents optionally substituted tetrahydropyranylpyridinyl-. In a fourth aspect of that embodiment, $R^1$ represents optionally substituted piperidinylpyridinyl-. In a fifth aspect of that embodiment, $R^1$ represents optionally substituted piperazinylpyridinyl-. In a sixth aspect of that embodiment, $R^1$ represents optionally substituted morpholinylpyridinyl-. In a seventh aspect of that embodiment, $R^1$ represents optionally substituted thiomorpholinylpyridinyl-. In an eighth aspect of that embodiment, $R^1$ represents optionally substituted diazepanylpyridinyl-. In a ninth aspect of that embodiment, $R^1$ represents optionally substituted oxetanylpyrimidinyl-. In a tenth aspect of that embodiment, $R^1$ represents optionally substituted azetidinylpyrimidinyl-. In an eleventh aspect of that embodiment, $R^1$ represents optionally substituted tetrahydrofuranylpyrimidinyl-. In a twelfth aspect of that embodiment, $R^1$ represents substituted tetrahydrothienyl-pyrimidinyl-. In a thirteenth aspect of that embodiment, $R^1$ represents optionally substituted pyrrolidinylpyrimidinyl-. In a fourteenth aspect of that embodiment, $R^1$ represents optionally substituted tetrahydropyranylpyrimidinyl-. In a fifteenth aspect of that embodiment, $R^1$ represents optionally substituted dioxanylpyrimidinyl-. In a sixteenth aspect of that embodiment, $R^1$ represents optionally substituted piperidinylpyrimidinyl-. In a seventeenth aspect of that embodiment, $R^1$ represents optionally substituted piperazinylpyrimidinyl-. In an eighteenth aspect of that embodiment, $R^1$ represents optionally substituted morpholinylpyrimidinyl-. In a nineteenth aspect of that embodiment, $R^1$ represents optionally substituted thiomorpholinylpyrimidinyl-. In a twentieth aspect of that embodiment, $R^1$ represents optionally substituted azepanylpyrimidinyl-. In a twenty-first aspect of that embodiment, $R^1$ represents optionally substituted oxazepanylpyrimidinyl-. In a twenty-second aspect of that embodiment, $R^1$ represents optionally substituted diazepanylpyrimidinyl-. In a twenty-third aspect of that embodiment, $R^1$ represents optionally substituted thiadiazepanylpyrimidinyl-. In a twenty-fourth aspect of that embodiment, $R^1$ represents optionally substituted oxetanylpyrazinyl-. In a twenty-fifth aspect of that embodiment, $R^1$ represents optionally substituted piperidinylpyrazinyl-.

In a twelfth embodiment, $R^1$ represents optionally substituted $(C_{4-9})$-heterobicycloalkyl-heteroaryl-. In a first aspect of that embodiment, $R^1$ represents optionally substituted (2-oxa-5-azabicyclo[2.2.1]heptanyl)pyrimidinyl-. In a second aspect of that embodiment, $R^1$ represents optionally substituted (3-oxa-8-azabicyclo-[3.2.1]octanyl)pyrimidinyl-. In a third aspect of that embodiment, $R^1$ represents optionally substituted (3,6-diazabicyclo[3.2.2]nonanyl)pyrimidinyl-. In a fourth aspect of that embodiment, $R^1$ represents optionally substituted (3,7-dioxa-9-azabicyclo[3.3.1]-nonanyl)pyrimidinyl-.

In a thirteenth embodiment, $R^1$ represents optionally substituted $(C_{4-9})$spiro-heterocycloalkyl-heteroaryl-.

Appositely, $R^1$ represents fluoro, chloro or cyano; or $R^1$ represents phenyl, azetidinyl, dihydropyridinyl, dihydropyrimidinyl, pyrazolyl, pyridinyl, pyrimidinyl, imidazolylphenyl, cyclopropylpyridinyl, cyclobutylpyridinyl, cyclobutylpyrimidinyl, cyclohexylpyrimidinyl, azetidinylpyrazolyl, oxetanylpyridinyl, azetidinylpyridinyl, pyrrolidinylpyridinyl, piperazinylpyridinyl, oxetanylpyrimidinyl, azetidinylpyrimidinyl, tetrahydrofuranylpyrimidinyl, tetrahydrothienylpyrimidinyl, pyrrolidinylpyrimidinyl, tetrahydropyranylpyrimidinyl, dioxanylpyrimidinyl, piperazinylpyrimidinyl, morpholinylpyrimidinyl, thiomorpholinylpyrimidinyl, diazepanylpyrimidinyl, (2-oxa-5-azabicyclo-[2.2.1]heptanyl)pyrimidinyl, (3-oxa-8-azabicyclo[3.2.1]octanyl)pyrimidinyl, (3,6-diazabicyclo[3.2.2]nonanyl)pyrimidinyl or (3,7-dioxa-9-azabicyclo[3.3.1]nonanyl)-pyrimidinyl, any of which groups may be optionally substituted by one or more substituents.

More typically, $R^1$ represents fluoro or chloro; or $R^1$ represents pyrimidinyl, cyclobutylpyrimidinyl, cyclopentylpyrimidinyl, cyclohexylpyrimidinyl, oxetanylpyrimidinyl, tetrahydrofuranylpyrimidinyl, pyrrolidinylpyrimidinyl, tetrahydropyranylpyrimidinyl, dioxanylpyrimidinyl or morpholinylpyrimidinyl, any of which groups may be optionally substituted by one or more substituents.

Still more typically, $R^1$ represents chloro; or $R^1$ represents pyrimidinyl, which group may be optionally substituted by one or more substituents.

Illustratively, $R^1$ represents pyrimidinyl, which group may be optionally substituted by one or more substituents.

Typical examples of optional substituents on $R^1$ include one, two or three substituents independently selected from halogen, halo$(C_{1-4})$alkyl, cyano, cyano$(C_{1-4})$alkyl, nitro$(C_{1-6})$alkyl, $C_{1-6}$ alkyl, phosphate$(C_{1-6})$alkyl, $(C_{1-6})$alkyl-phosphate$(C_{1-4})$alkyl, phosphate$(C_{1-6})$alkoxy$(C_{1-6})$alkyl, sulphate$(C_{1-6})$alkyl, difluoromethyl, trifluoromethyl, trifluoroethyl, $C_{2-6}$ alkenyl, hydroxy, hydroxy$(C_{1-6})$alkyl, $C_{1-6}$ alkoxy, $(C_{1-6})$alkoxy$(C_{1-6})$-alkyl, trifluoroethoxy, carboxy$(C_{3-7})$cycloalkyloxy, $C_{1-6}$ alkylthio, $C_{1-6}$ alkylsulphonyl, $(C_{1-6})$alkylsulphonyl$(C_{1-6})$alkyl, oxo, amino, amino$(C_{1-4})$alkyl, $C_{1-6}$ alkylamino, di$(C_{1-6})$-alkylamino, di$(C_{1-6})$alkylamino$(C_{1-6})$alkyl, $(C_{1-6})$alkoxy$(C_{1-6})$alkylamino, N—[$(C_{1-6})$alkyl]-N-[hydroxy$(C_{1-6})$alkyl]amino, $(C_{2-4})$alkylcarbonylamino$(C_{1-6})$alkyl, $(C_{2-6})$alkoxycarbonyl-amino$(C_{1-6})$alkyl, $C_{1-6}$ alkylsulphinylamino, $C_{1-6}$ alkylsulphonylamino, N—[(C$_{1-6}$)alkyl]-N—[(C$_{1-6}$)alkylsulphonyl]amino, bis [(C$_{1-6}$)alkylsulphonyl]amino, (C$_{1-6}$)alkylsulphonylamino-(C$_{1-6}$)alkyl, N—[(C$_{1-6}$)alkyl]-N-[carboxy(C$_{1-6}$)alkyl]amino, carboxy(C$_{3-7}$)cycloalkylamino, carboxy(C$_{3-7}$)cycloalkyl (C$_{1-6}$)alkylamino, imino, formyl, C$_{2-6}$ alkylcarbonyl, (C$_{2-6}$) alkyl-carbonyloxy(C$_{1-6}$)alkyl, carboxy, carboxy(C$_{1-6}$)alkyl, C$_{2-6}$ alkoxycarbonyl, C$_{2-6}$ alkoxy-carbonyl(C$_{1-6}$)alkyl, morpholinyl(C$_{1-6}$)alkoxycarbonyl, C$_{2-6}$ alkoxycarbonylmethylidenyl, aminocarbonyl, aminosulphonyl, (C$_{1-6}$)alkylsulphoximinyl and [(C$_{1-6}$)alkyl][N—(C$_{1-6}$)-alkyl]sulphoximinyl.

Illustrative examples of optional substituents on R$^1$ include one, two or three substituents independently selected from halogen, cyano, C$_{1-6}$ alkyl, difluoromethyl, hydroxy (C$_{1-6}$)alkyl, oxo, amino and amino(C$_{1-6}$)alkyl.

Particular examples of optional substituents on R$^1$ include one, two or three substituents independently selected from hydroxy(C$_{1-4}$)alkyl and amino(C$_{1-6}$)alkyl.

Typical examples of particular substituents on R$^1$ include one, two or three substituents independently selected from fluoro, chloro, fluoromethyl, fluoroisopropyl, cyano, cyanoethyl, cyanoisopropyl, nitromethyl, methyl, ethyl, isopropyl, isopropylmethyl, phosphate-isopropyl, ethylphosphate-isopropyl, phosphate-methoxyisopropyl, sulphate-isopropyl, difluoromethyl, trifluoromethyl, trifluoroethyl, ethenyl, hydroxy, hydroxymethyl, hydroxyisopropyl, hydroxyisobutyl, methoxy, isopropoxy, methoxyisopropyl, trifluoroethoxy, carboxycyclobutyloxy, methylthio, methylsulphonyl, methyl-sulphonylmethyl, methylsulphonylethyl, oxo, amino, aminomethyl, aminoisopropyl, methylamino, dimethylamino, dimethylaminoisopropyl, methoxyethylamino, N-(hydroxyethyl)-N-(methyl)amino, acetylaminomethyl, acetylaminoisopropyl, methoxy-carbonylaminoisopropyl, (tert-butoxycarbonyl)aminoisopropyl, (tert-butyl)sulphinylamino, methylsulphonylamino, (tert-butyl)sulphonylamino, N-methyl-N-(methyl-sulphonyl)amino, bis(methylsulphonyl)amino, methylsulphonylaminoisopropyl, N-(carboxyethyl)-N-(methyl)amino, carboxycyclopentylamino, carboxycyclopropylmethyl-amino, imino, formyl, acetyl, (tert-butyl)carbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, aminocarbonyl, aminosulphonyl, methylsulphoximinyl and (methyl)(N-methyl)sulphoximinyl.

Illustrative examples of particular substituents on R$^1$ include one, two or three substituents independently selected from fluoro, cyano, methyl, difluoromethyl, hydroxyisopropyl, oxo, amino and aminoisopropyl.

Suitable examples of particular substituents on R$^1$ include one, two or three substituents independently selected from hydroxyisopropyl and aminoisopropyl.

In a particular embodiment, R$^1$ is substituted by hydroxy (C$_{1-6}$)alkyl. In one aspect of that embodiment, R$^1$ is substituted by hydroxyisopropyl, especially 2-hydroxyprop-2-yl.

In another embodiment, R$^1$ is substituted by amino(C$_{1-6}$) alkyl. In one aspect of that embodiment, R$^1$ is substituted by aminoisopropyl, especially 2-aminoprop-2-yl.

Illustrative values of R$^1$ include fluoro, chloro, cyano, (methyl)(methylthio)phenyl, methylsulphonylphenyl, (methylxmethylsulphonyl)phenyl, methylsulphoximinylphenyl, (hydroxyisopropyl)azetidinyl, methylpyrazolyl, hydroxyisopropylpyridinyl, (hydroxyisopropyl)(methyl) pyridinyl, methoxypyridinyl, oxopyridinyl, (methyl)(oxo)-pyridinyl, cyanoisopropylpyrimidinyl, phosphate-isopropylpyrimidinyl, sulphate-isopropylpyrimidinyl, hydroxyisopropylpyrimidinyl, (hydroxyisopropyl)(methyl)-pyrimidinyl, (dimethyl)(hydroxyisopropyl)pyrimidinyl, (difluoromethyl)-(hydroxyisopropyl)pyrimidinyl, (hydroxyisopropyl)(trifluoromethyl)pyrimidinyl, hydroxyisobutylpyrimidinyl, methoxyisopropylpyrimidinyl, oxopyrimidinyl, amino isopropylpyrimidinyl, (dimethylamino)isopropylpyrimidinyl, acetylaminoisopropyl-pyrimidinyl, (methoxycarbonyl)aminoisopropylpyrimidinyl, (tert-butoxycarbonyl)aminoisopropylpyrimidinyl, (methylsulphonyl)aminoisopropylpyrimidinyl, methyl-sulphoximinylpyridinyl, (dimethyl)imidazolylphenyl, methylsulphonylcyclopropyl-pyridinyl, aminocyclobutylpyridinyl, (tert-butyl)sulphinylaminocyclobutylpyridinyl, (dihydroxy) (methyl)cyclobutylpyrimidinyl, aminocyclobutylpyrimidinyl, (amino)(cyano)-cyclobutylpyrimidinyl, (amino)difluoromethyl)cyclobutylpyrimidinyl, aminocyclopentylpyrimidinyl, (difluoro)(hydroxy)cyclohexylpyrimidinyl, (dihydroxy)(methyl)cyclohexylpyrimidinyl, (amino)difluoro)cyclohexylpyrimidinyl, (methylsulphonyl)azetidinylpyrazolyl, aminooxetanylpyridinyl, (tert-butyl)sulphinylaminooxetanylpyridinyl, (tert-butyl) sulphonylaminooxetanylpyridinyl, pyrrolidinylpyridinyl, (hydroxy)pyrrolidinylpyridinyl, (tert-butoxycarbonyl)(hydroxy)pyrrolidinylpyridinyl, piperazinylpyridinyl, (methylsulphonyl)piperazinylpyridinyl, (hydroxy)oxetanylpyrimidinyl, (amino)oxetanylpyrimidinyl, (difluoro) azetidinylpyrimidinyl, (cyano)(methyl) azetidinylpyrimidinyl, (hydroxy)(methyl) azetidinylpyrimidinyl, (hydroxy)(trifluoromethyl) azetidinylpyrimidinyl, [(hydroxytrifluoromethyl)azetidinyl] (methyl)pyrimidinyl, (hydroxyisopropyl)-(tetrahydrofuranyl)pyrimidinyl, aminotetrahydrofuranylpyrimidinyl, (hydroxy)-tetrahydrothienylpyrimidinyl, (hydroxy)(oxo)tetrahydrothienylpyrimidinyl, (hydroxy)-(dioxo)tetrahydrothienylpyrimidinyl, pyrrolidinylpyrimidinyl, methylpyrrolidinyl-pyrimidinyl, tetrahydropyranylpyrimidinyl, aminotetrahydropyranylpyrimidinyl, (amino)dimethyl)dioxanylpyrimidinyl, (hydroxyisopropyl)piperidinylpyrimidinyl, (aminoisopropyl)piperidinylpyrimidinyl, (oxo)piperazinylpyrimidinyl, morpholinylpyrimidinyl, methylmorpholinylpyrimidinyl, aminomorpholinylpyrimidinyl, thiomorpholinylpyrimidinyl, (oxo)thiomorpholinylpyrimidinyl, (dioxo)thiomorpholinylpyrimidinyl, (amino)dioxo)thiomorpholinylpyrimidinyl, (oxo)diazepanylpyrimidinyl, hydroxyisopropyl-(3-azabicyclo[3.1.0]hexanyl)pyrimidinyl, (2-oxa-5-azabicyclo[2.2.1]-heptanyl)pyrimidinyl, (3-oxa-8-azabicyclo[3.2.1] octanyl)pyrimidinyl, (oxo)(3,6-diazabicyclo[3.2.2]nonanyl) pyrimidinyl and (3,7-dioxa-9-azabicyclo[3.3.1]nonanyl)-pyrimidinyl.

Typical values of R$^1$ include fluoro, chloro, hydroxyisopropylpyrimidinyl, aminoisopropylpyrimidinyl, aminocyclobutylpyrimidinyl, (amino)(cyano)cyclobutylpyrimidinyl, (amino)(difluoromethyl)cyclobutylpyrimidinyl, aminocyclopentyl-pyrimidinyl, (amino)difluoro)cyclohexylpyrimidinyl, (amino)oxetanylpyrimidinyl, aminotetrahydrofuranylpyrimidinyl, pyrrolidinylpyrimidinyl, methylpyrrolidinyl-pyrimidinyl, aminotetrahydropyranylpyrimidinyl, (amino)dimethyl)dioxanylpyrimidinyl, (hydroxyisopropyl)piperidinylpyrimidinyl, (amino isopropyl) piperidinylpyrimidinyl, morpholinylpyrimidinyl, methylmorpholinylpyrimidinyl, aminomorpholinylpyrimidinyl, (dioxo)thiomorpholinylpyrimidinyl, (amino)dioxo) thiomorpholinylpyrimidinyl and hydroxyisopropyl-(3-azabicyclo[3.1.0]hexanyl)pyrimidinyl.

Selected values of R$^1$ include chloro, hydroxyisopropylpyrimidinyl and aminoisopropylpyrimidinyl.

In a particular embodiment, $R^1$ represents hydroxyisopropylpyrimidinyl, especially 2-(2-hydroxypropan-2-yl)pyrimidin-5-yl.

In another embodiment, $R^1$ represents aminoisopropylpyrimidinyl, especially 2-(2-aminopropan-2-yl)pyrimidin-5-yl.

Generally, $R^2$ represents hydrogen, halogen, trifluoromethyl, trifluoromethoxy or —$OR^a$; or $R^2$ represents $C_{1-6}$ alkyl or heteroaryl, either of which groups may be optionally substituted by one or more substituents.

Typically, $R^2$ represents hydrogen or halogen; or $R^2$ represents heteroaryl, which group may be optionally substituted by one or more substituents.

Appositely, $R^2$ represents halogen; or $R^2$ represents heteroaryl, which group may be optionally substituted by one or more substituents.

Suitably, $R^2$ represents hydrogen or halogen.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —$OR^a$. In a ninth embodiment, $R^2$ represents optionally substituted $C_{1-6}$ alkyl. In a first aspect of that embodiment, $R^2$ represents methyl. In a second aspect of that embodiment, $R^2$ represents ethyl. In a tenth embodiment, $R^2$ represents optionally substituted heteroaryl. In a first aspect of that embodiment, $R^2$ represents optionally substituted pyrimidinyl.

Typical examples of optional substituents on $R^2$ include one, two or three substituents independently selected from hydroxy($C_{1-4}$)alkyl and $C_{2-6}$ alkoxycarbonyl.

Suitable examples of optional substituents on $R^2$ include one, two or three substituents independently selected from hydroxy($C_{1-4}$)alkyl.

Typical examples of particular substituents on $R^2$ include one, two or three substituents independently selected from hydroxyisopropyl and ethoxycarbonyl.

Suitable examples of particular substituents on $R^2$ include one, two or three substituents independently selected from hydroxyisopropyl.

Typical values of $R^2$ include hydrogen, fluoro, chloro, trifluoromethyl, trifluoromethoxy, —$OR^a$, methyl, ethoxycarbonylethyl and hydroxyisopropylpyrimidinyl.

Illustrative values of $R^2$ include hydrogen and fluoro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents optionally substituted $C_{1-6}$ alkyl. In one aspect of that embodiment, $R^3$ represents methyl. In another aspect of that embodiment, $R^3$ represents ethyl.

Typically, $R^4$ represents hydrogen, halogen or $C_{1-6}$ alkyl.

In a first embodiment, $R^4$ represents hydrogen. In a second embodiment, $R^4$ represents halogen. In one aspect of that embodiment, $R^4$ represents fluoro. In a third embodiment, $R^4$ represents optionally substituted $C_{1-6}$ alkyl. In one aspect of that embodiment, $R^4$ represents methyl. In another aspect of that embodiment, $R^4$ represents ethyl.

Generally, $R^5$ represents halogen, cyano, difluoromethoxy, trifluoromethoxy, —$OR^a$ or $C_{1-6}$ alkylsulphonyl; or $R^5$ represents $C_{1-6}$ alkyl, which group may be optionally substituted by one or more substituents.

Typically, $R^5$ represents difluoromethoxy or —$OR^a$.

In a first embodiment, $R^5$ represents hydrogen. In a second embodiment, $R^5$ represents halogen. In one aspect of that embodiment, $R^5$ represents fluoro. In another aspect of that embodiment, $R^5$ represents chloro. In a third embodiment, $R^5$ represents hydroxy. In a fourth embodiment, $R^5$ represents cyano. In a fifth embodiment, $R^5$ represents trifluoromethyl. In a sixth embodiment, $R^5$ represents difluoromethoxy. In a seventh embodiment, $R^5$ represents trifluoromethoxy. In an eighth embodiment, $R^5$ represents —$OR^a$. In one aspect of that embodiment, $R^5$ represents methoxy. In a ninth embodiment, $R^5$ represents $C_{1-6}$ alkylsulphonyl. In one aspect of that embodiment, $R^5$ represents methylsulphonyl. In a tenth embodiment, $R^5$ represents optionally substituted $C_{1-6}$ alkyl. In one aspect of that embodiment, $R^5$ represents methyl. In another aspect of that embodiment, $R^5$ represents ethyl.

Appositely, $R^5$ represents difluoromethoxy or methoxy.

Generally, $R^6$ represents hydrogen, halogen or trifluoromethyl.

In a first embodiment, $R^6$ represents hydrogen. In a second embodiment, $R^6$ represents halogen. In one aspect of that embodiment, $R^6$ represents fluoro. In another aspect of that embodiment, $R^6$ represents chloro. In a third embodiment, $R^6$ represents trifluoromethyl. In a fourth embodiment, $R^6$ represents $C_{1-6}$ alkyl. In one aspect of that embodiment, $R^6$ represents methyl. In another aspect of that embodiment, $R^6$ represents ethyl. In a fifth embodiment, $R^6$ represents $C_{1-6}$ alkoxy. In one aspect of that embodiment, $R^6$ represents methoxy.

Generally, $R^7$ represents hydrogen or trifluoromethyl.

In a first embodiment, $R^7$ represents hydrogen. In a second embodiment, $R^7$ represents halogen. In one aspect of that embodiment, $R^7$ represents fluoro. In another aspect of that embodiment, $R^7$ represents chloro. In a third embodiment, $R^7$ represents trifluoromethyl. In a fourth embodiment, $R^7$ represents $C_{1-6}$ alkyl. In one aspect of that embodiment, $R^7$ represents methyl. In another aspect of that embodiment, $R^7$ represents ethyl. In a fifth embodiment, $R^7$ represents $C_{1-6}$ alkoxy. In one aspect of that embodiment, $R^7$ represents methoxy.

Generally, $R^8$ represents hydrogen or trifluoromethyl.

In a first embodiment, $R^8$ represents hydrogen. In a second embodiment, $R^8$ represents halogen. In one aspect of that embodiment, $R^8$ represents fluoro. In another aspect of that embodiment, $R^8$ represents chloro. In a third embodiment, $R^8$ represents trifluoromethyl. In a fourth embodiment, $R^8$ represents $C_{1-6}$ alkyl. In one aspect of that embodiment, $R^8$ represents methyl. In another aspect of that embodiment, $R^8$ represents ethyl. In a fifth embodiment, $R^8$ represents $C_{1-6}$ alkoxy. In one aspect of that embodiment, $R^8$ represents methoxy.

Typically, $R^{12}$ represents hydrogen or methyl.

In a first embodiment, $R^{12}$ represents hydrogen. In a second embodiment, $R^{12}$ represents $C_{1-6}$ alkyl. In one aspect of that embodiment, $R^{12}$ represents methyl. In another aspect of that embodiment, $R^{12}$ represents ethyl.

Typical examples of suitable substituents which may be present on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkyl-sulphonylamino, aminocarbonyl, $C_{1-6}$ alkylaminocarbonyl and di($C_{1-6}$)alkylaminocarbonyl.

Typical examples of specific substituents which may be present on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl.

In another embodiment, $R^a$ represents optionally substituted aryl($C_{1-6}$)alkyl, ideally unsubstituted aryl($C_{1-4}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-4}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl, Suitably, $R^c$ represents hydrogen or $C_{1-6}$ alkyl. In one embodiment, $R^c$ is hydrogen.

In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonyl-amino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —NR$^b$R$^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethyl-piperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, R$^d$ represents hydrogen; or C$_{1-6}$ alkyl, aryl or heteroaryl, any of which groups may be optionally substituted by one or more substituents.

Selected examples of suitable values for R$^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on R$^d$ include halogen, C$_{1-6}$ alkyl, C$_{1-6}$ alkoxy, oxo, C$_{2-6}$ alkylcarbonyloxy and di(C$_{1-6}$)alkylamino.

Selected examples of particular substituents on R$^d$ include fluoro, methyl, methoxy, oxo, acetoxy and dimethylamino.

In one embodiment, R$^d$ represents hydrogen. In another embodiment, R$^d$ represents optionally substituted C$_{1-6}$ alkyl. In one aspect of that embodiment, R$^d$ ideally represents unsubstituted C$_{1-6}$ alkyl, e.g. methyl, ethyl, isopropyl, 2-methylpropyl or tert-butyl, especially methyl. In another aspect of that embodiment, R$^d$ ideally represents substituted C$_{1-6}$ alkyl, e.g. substituted methyl or substituted ethyl, including acetoxymethyl, dimethylaminomethyl and trifluoroethyl. In another embodiment, R$^d$ represents optionally substituted aryl. In one aspect of that embodiment, R$^d$ represents unsubstituted aryl, especially phenyl. In another aspect of that embodiment, R$^d$ represents monosubstituted aryl, especially methylphenyl. In a further aspect of that embodiment, R$^d$ represents disubstituted aryl, e.g. dimethoxyphenyl. In a further embodiment, R$^d$ represents optionally substituted heteroaryl, e.g. thienyl, chlorothienyl, methylthienyl, methylimidazolyl or thiazolyl. In another embodiment, R$^d$ represents optionally substituted C$_{3-7}$ cycloalkyl, e.g. cyclopropyl or cyclobutyl. In a further embodiment, R$^d$ represents optionally substituted C$_{3-7}$ heterocycloalkyl, e.g. thiazolidinyl or oxothiazolidinyl.

Selected examples of specific values for R$^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, R$^e$ represents C$_{1-6}$ alkyl or aryl, either of which groups may be optionally substituted by one or more substituents.

Selected examples of suitable substituents on R$^e$ include C$_{1-6}$ alkyl, especially methyl.

In one embodiment, R$^e$ represents optionally substituted C$_{1-6}$ alkyl, ideally unsubstituted C$_{1-6}$ alkyl, e.g. methyl or propyl, especially methyl. In another embodiment, R$^e$ represents optionally substituted aryl. In one aspect of that embodiment, R$^e$ represents unsubstituted aryl, especially phenyl. In another aspect of that embodiment, R$^e$ represents monosubstituted aryl, especially methylphenyl. In a further embodiment, R$^e$ represents optionally substituted heteroaryl.

Selected values of R$^e$ include methyl, propyl and methylphenyl.

Suitably, R$^f$ represents hydrogen or methyl.

In a first embodiment, R$^f$ represents hydrogen. In a second embodiment, R$^f$ represents C$_{1-6}$ alkyl, especially methyl.

Suitably, R$^g$ represents hydrogen or methyl.

In a first embodiment, R$^g$ represents hydrogen. In a second embodiment, R$^g$ represents C$_{1-6}$ alkyl, especially methyl.

One sub-group of the compounds of formula (IB) above is represented by the compounds of formula (IIA) and N-oxides thereof, and pharmaceutically acceptable salts thereof:

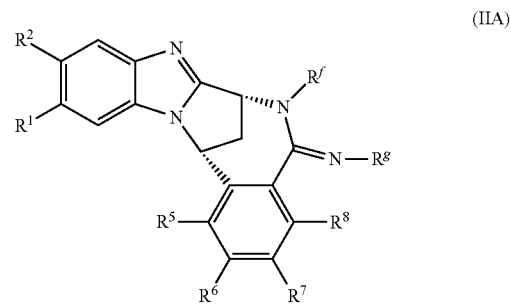

(IIA)

wherein R$^1$, R$^2$, R$^5$, R$^6$, R$^7$, R$^8$, R$^f$ and R$^g$ are as defined above.

A particular subset of the compounds of formula (IIA) above is represented by the compounds of formula (IIA-1) and N-oxides thereof, and pharmaceutically acceptable salts thereof:

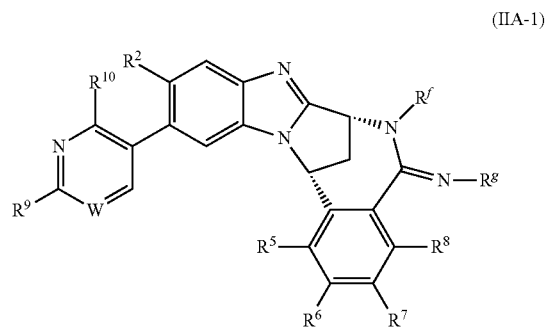

(IIA-1)

wherein
W represents N, CH or CF;
R$^9$ represents hydroxy(C$_{1-6}$)alkyl or amino(C$_{1-6}$)alkyl;
R$^{10}$ represents hydrogen or C$_{1-6}$ alkyl; and
R$^2$, R$^5$, R$^6$, R$^7$, R$^8$, R$^f$ and R$^g$ are as defined above.
Generally, W represents N or CH.
Suitably, W represents N or CF.
In one embodiment, W represents N. In another embodiment, W represents CH. In a further embodiment, W represents CF.
Typically, R$^9$ represents hydroxyisopropyl or aminoisopropyl.
Typical values of R$^9$ include 2-hydroxyprop-2-yl and 2-aminoprop-2-yl.

In one embodiment, $R^9$ represents hydroxy($C_{1-6}$)alkyl. In a particular aspect of that embodiment, $R^9$ represents hydroxyisopropyl, especially 2-hydroxyprop-2-yl.

In another embodiment, $R^9$ represents amino($C_{1-6}$)alkyl. In a particular aspect of that embodiment, $R^9$ represents aminoisopropyl, especially 2-aminoprop-2-yl.

Typically, $R^{10}$ represents hydrogen or methyl.

In one embodiment, $R^{10}$ represents hydrogen. In another embodiment, $R^{10}$ represents $C_{1-6}$ alkyl. In one aspect of that embodiment, $R^{10}$ represents methyl.

Another subset of the compounds of formula (IIA) above is represented by the compounds of formula (IIA-2) and N-oxides thereof, and pharmaceutically acceptable salts thereof:

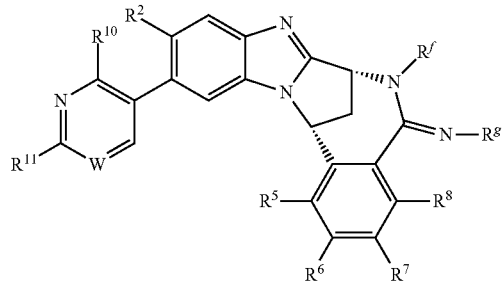
(IIA-2)

wherein
$R^{11}$ represents a group of formula (a), (b), (c), (d), (e), (f) or (g):

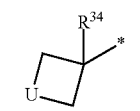
(a)

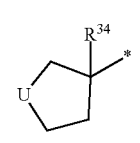
(b)

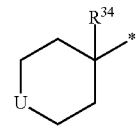
(c)

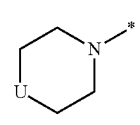
(d)

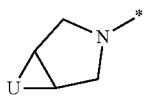
(e)

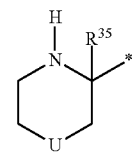
(f)

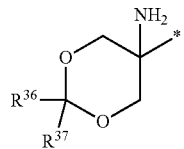
(g)

in which the asterisk (*) represents the site of attachment to the remainder of the molecule;

U represents O, S, S(O), S(O)$_2$, S(O)(NR$^b$), N(R$^{31}$) or C(R$^{32}$)(R$^{33}$);

$R^{31}$ represents hydrogen, cyano($C_{1-6}$)alkyl, $C_{1-6}$ alkyl, trifluoromethyl, trifluoroethyl, $C_{1-6}$ alkylsulphonyl, ($C_{1-6}$)alkylsulphonyl($C_{1-6}$)alkyl, formyl, $C_{2-6}$ alkylcarbonyl, carboxy, carboxy($C_{1-6}$)alkyl, $C_{2-6}$ alkoxycarbonyl, $C_{2-6}$ alkoxycarbonyl($C_{1-6}$)alkyl, tetrazolyl($C_{1-6}$)alkyl, aminocarbonyl, $C_{1-6}$ alkylaminocarbonyl, di($C_{1-6}$)alkylaminocarbonyl, aminosulphonyl, $C_{1-6}$ alkylaminosulphonyl or di($C_{1-6}$)alkylaminosulphonyl;

$R^{32}$ represents hydrogen, halogen, cyano, hydroxy, hydroxy($C_{1-6}$)alkyl, $C_{1-6}$ alkylsulphonyl, formyl, carboxy, carboxy($C_{1-6}$)alkyl, $C_{2-6}$ alkoxycarbonyl, $C_{2-6}$ alkoxycarbonyl($C_{1-6}$)alkyl, aminosulphonyl, ($C_{1-6}$)alkylsulphoximinyl, [($C_{1-6}$)alkyl][N—($C_{1-6}$)alkyl]sulphoximinyl, ($C_{1-6}$)alkylsulphonylaminocarbonyl, ($C_{2-6}$)alkylcarbonylamino-sulphonyl, ($C_{1-6}$)alkoxyaminocarbonyl, tetrazolyl or hydroxyoxadiazolyl;

$R^{33}$ represents hydrogen, halogen, $C_{1-6}$ alkyl, difluoromethyl, trifluoromethyl, hydroxy, hydroxy($C_{1-6}$)alkyl, $C_{1-6}$ alkoxy, amino or carboxy;

$R^{34}$ represents hydrogen, halogen, halo($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, amino, $C_{1-6}$ alkylamino, di($C_{1-6}$)alkylamino, ($C_{2-6}$)alkylcarbonylamino, ($C_{2-6}$)alkylcarbonylamino($C_{1-6}$)alkyl, ($C_{1-6}$)alkyl-sulphonylamino or ($C_{1-6}$)alkylsulphonylamino($C_{1-6}$)alkyl;

$R^{35}$ represents hydrogen or $C_{1-6}$ alkyl;

$R^{36}$ and $R^{37}$ independently represent $C_{1-6}$ alkyl; or $R^{36}$ and $R^{37}$, when taken together with the carbon atom to which they are both attached, represent $C_{3-7}$ cycloalkyl; and W, $R^2$, $R^5$, $R^6$, $R^7$, $R^8$, $R^{10}$, $R^b$, $R^f$ and $R^g$ are as defined above.

Generally, U represents O, S(O)$_2$, N(R$^{31}$) or C(R$^{32}$)(R$^{33}$).

Typically, U represents O, N(R$^{31}$) or C(R$^{32}$)(R$^{33}$).

In a first embodiment, U represents O. In a second embodiment, U represents S. In a third embodiment, U represents S(O). In a fourth embodiment, U represents S(O)$_2$. In a fifth embodiment, U represents S(O)(NR$^b$). In a sixth embodiment, U represents N(R$^{31}$). In a seventh embodiment, U represents C(R$^{32}$)(R$^{33}$).

Typical values of $R^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolylmethyl, aminocarbonyl, methylaminocarbonyl, dimethylaminocarbonyl, aminosulphonyl, methylaminosulphonyl and dimethylaminosulphonyl.

Suitably, $R^{31}$ represents hydrogen or $C_{1-6}$ alkyl.

Suitable values of $R^{31}$ include hydrogen and methyl.

In a first embodiment, $R^{31}$ represents hydrogen. In a second embodiment, $R^{31}$ represents $C_{1-6}$ alkyl, especially methyl.

Typical values of $R^{32}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, acetylaminosulphonyl, methoxyaminocarbonyl, tetrazolyl and hydroxyoxadiazolyl.

Suitably, $R^{32}$ represents hydrogen, halogen or cyano.

Suitable values of $R^{32}$ include hydrogen, fluoro and cyano.

In a first embodiment, $R^{32}$ represents hydrogen. In a second embodiment, $R^{32}$ represents halogen, especially fluoro. In a third embodiment, $R^{32}$ represents cyano.

Generally, $R^{33}$ represents hydrogen, halogen, $C_{1-6}$ alkyl, difluoromethyl or trifluoromethyl.

Typical values of $R^3$ include hydrogen, fluoro, methyl, ethyl, isopropyl, difluoromethyl, trifluoromethyl, hydroxy, hydroxymethyl, methoxy, amino and carboxy.

Suitably, $R^{33}$ represents hydrogen, halogen or difluoromethyl.

Suitable values of $R^{33}$ include hydrogen, fluoro and difluoromethyl.

In a first embodiment, $R^{33}$ represents hydrogen. In a second embodiment, $R^3$ represents halogen. In one aspect of that embodiment, $R^{33}$ represents fluoro. In a third embodiment, $R^{33}$ represents $C_{1-6}$ alkyl. In a first aspect of that embodiment, $R^{33}$ represents methyl. In a second aspect of that embodiment, $R^{33}$ represents ethyl. In a third aspect of that embodiment, $R^{33}$ represents isopropyl. In a fourth embodiment, $R^{33}$ represents difluoromethyl. In a fifth embodiment, $R^{33}$ represents trifluoromethyl. In a sixth embodiment, $R^{33}$ represents hydroxy. In a seventh embodiment, $R^{33}$ represents hydroxy($C_{1-6}$)alkyl. In one aspect of that embodiment, $R^{33}$ represents hydroxymethyl. In an eighth embodiment, $R^{33}$ represents $C_{1-6}$ alkoxy. In one aspect of that embodiment, $R^{33}$ represents methoxy. In a ninth embodiment, $R^{33}$ represents amino. In a tenth embodiment, $R^{33}$ represents carboxy.

In a first embodiment, $R^{34}$ represents hydrogen. In a second embodiment, $R^{34}$ represents halogen. In one aspect of that embodiment, $R^{34}$ represents fluoro. In a third embodiment, $R^{34}$ represents halo($C_{1-4}$)alkyl. In one aspect of that embodiment, $R^4$ represents fluoromethyl. In a fourth embodiment, $R^{34}$ represents hydroxy. In a fifth embodiment, $R^{34}$ represents $C_{1-6}$ alkoxy, especially methoxy. In a sixth embodiment, $R^{34}$ represents $C_{1-6}$ alkylthio, especially methylthio. In a seventh embodiment, $R^{34}$ represents $C_{1-6}$ alkylsulphinyl, especially methylsulphinyl. In an eighth embodiment, $R^{34}$ represents $C_{1-6}$ alkylsulphonyl, especially methylsulphonyl. In a ninth embodiment, $R^{34}$ represents amino. In a tenth embodiment, $R^{34}$ represents $C_{1-6}$ alkylamino, especially methylamino. In an eleventh embodiment, $R^{34}$ represents di($C_{1-6}$)alkylamino, especially dimethylamino. In a twelfth embodiment, $R^{34}$ represents $(C_{2-4})$alkylcarbonylamino, especially acetylamino. In a thirteenth embodiment, $R^4$ represents $(C_{2-4})$alylcarbonylamino($C_{1-6}$)alkyl, especially acetylaminomethyl. In a fourteenth embodiment, $R^{34}$ represents $(C_{1-6})$alkylsulphonylamino, especially methylsulphonylamino. In a fifteenth embodiment, $R^4$ represents $(C_{1-6})$alkylsulphonylamino($C_{1-6}$)alkyl, especially methylsulphonylaminomethyl.

Suitably, $R^{34}$ represents hydrogen or amino.

Suitable values of $R^{35}$ include hydrogen and methyl.

In a first embodiment, $R^{35}$ represents hydrogen. In a second embodiment, $R^{35}$ represents $C_{1-6}$ alkyl, especially methyl.

Suitably, $R^{36}$ represents methyl or ethyl, especially methyl.

Suitably, $R^{37}$ represents methyl or ethyl, especially methyl.

Alternatively, $R^{36}$ and $R^{37}$, when taken together with the carbon atom to which they are both attached, may suitably represent cyclopropyl, cyclobutyl, cyclopentyl, cyclohexyl or cycloheptyl.

Specific novel compounds in accordance with the present invention include each of the compounds whose preparation is described in the accompanying Examples, and pharmaceutically acceptable salts thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis and inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behret's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy), organ transplant rejection (including kidney allograft rejection), scleritis (including giant cell arteritis scleritis), Takayasu arteritis, hidradenitis suppurativa, pyoderma gangrenosum, sarcoidosis, polymyalgia rheumatic and axial spondyloarthritis.

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above wherein $R^f$ and $R^g$ both represent hydrogen may be prepared by a process which comprises treating a compound of formula (III):

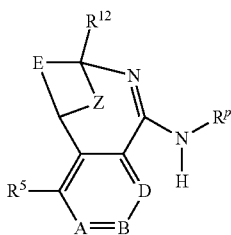

(III)

wherein A, B, D, Z, E, $R^5$ and $R^{12}$ are as defined above, and $R^p$ represents $C_{4-9}$ alkyl; with an acid.

Suitable values for the $C_{4-9}$ alkyl group $R^p$ include tert-butyl and 1,1,3,3-tetramethylbutyl. In a first embodiment, $R^p$ represents tert-butyl. In a second embodiment, $R^p$ represents 1,1,3,3-tetramethylbutyl.

The reaction is suitably effected by treating compound (III) with a mineral acid, e.g. hydrochloric acid, or an organic acid, e.g. trifluoroacetic acid, or a mixture thereof. The reaction may be conveniently carried out at an elevated temperature in a suitable solvent, e.g. a cyclic ether such as 1,4-dioxane.

The intermediates of formula (III) above may be prepared by reacting a compound of formula (IV):

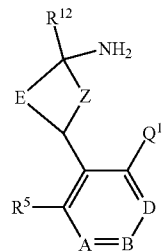

(IV)

wherein A, B, D, Z, E, $R^5$ and $R^{12}$ are as defined above, and $Q^1$ represents halogen; with an isocyanide derivative of formula $R^p$—NC, in the presence of a transition metal catalyst.

Suitably, $Q^1$ represents chloro or bromo.

The transition metal catalyst of use in the above reaction will suitably comprise a mixture of palladium(II) acetate and 1,1'-bis(diphenylphosphino)ferrocene. The reaction will conveniently be effected at an elevated temperature in a suitable solvent, e.g. a hydrocarbon solvent such as toluene. Moreover, the reaction will generally be performed in the presence of a base, e.g. an inorganic base such as cesium carbonate.

The intermediates of formula (IV) may be prepared from the intermediates of formula (V):

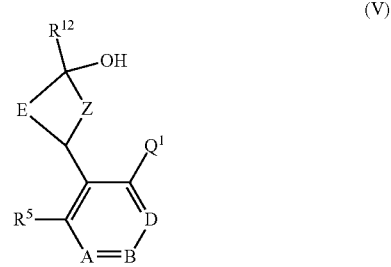

(V)

wherein A, B, D, Z, E, $R^5$, $R^{12}$ and $Q^1$ are as defined above; by a two-step procedure which comprises: (i) reaction with diphenyl phosphoryl azide; and (ii) reaction of the compound thereby obtained with trimethylphosphine.

Step (i) of the above procedure is suitably accomplished under basic conditions, e.g. in the presence of an organic base such as 1,8-diazabicyclo[5.4.0]undec-7-ene (DBU). The reaction is conveniently effected at an elevated temperature in a suitable organic solvent, e.g. a hydrocarbon solvent such as toluene.

Step (ii) of the above procedure is conveniently effected at ambient temperature in a suitable organic solvent, e.g. a mixture of tetrahydrofuran and toluene, and water.

The intermediates of formula (V) wherein E represents a group of formula (Ea) as defined above, and $R^{12}$ represents hydrogen, may be prepared by a process which comprises the intramolecular cyclization and desilylation of an intermediate of formula (VI):

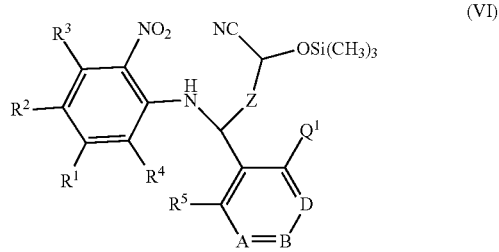

(VI)

wherein A, B, D, Z, $R^1$, $R^2$, $R^3$, $R^4$, $R^5$ and $Q^1$ are as defined above.

The reaction is suitably performed in the presence of tin(II) chloride at an elevated temperature in a polar solvent, e.g. ethanol.

The intermediates of formula (VI) as defined above may be prepared by reacting intermediate (VII):

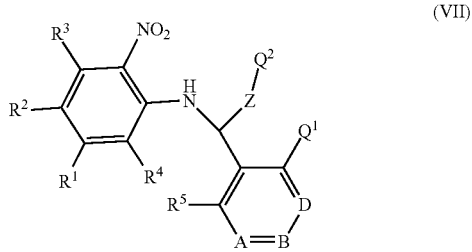

(VII)

wherein $Q^2$ represents —C(O)—H, and A, B, D, Z, $R^1$, $R^2$, $R^3$, $R^4$, $R^5$ and $Q^1$ are as defined above; with zinc iodide and trimethylsilyl cyanide in the presence of a base, e.g. triethylamine.

Typically, the intermediate of formula (VII) wherein $Q^2$ represents —C(O)—H may be prepared from the corresponding compound wherein $Q^2$ represents —CO$_2R^h$, in which $R^h$ represents $C_{1-6}$ alkyl, e.g. methyl or ethyl, by reduction with a conventional reducing agent, e.g. a metal hydride such as diisobutylaluminium hydride (DIBAL-H).

The intermediates of formula (VII) wherein $Q^2$ represents —CO$_2R^h$ may be obtained by reacting an intermediate of formula (VIII) with an intermediate of formula (IX):

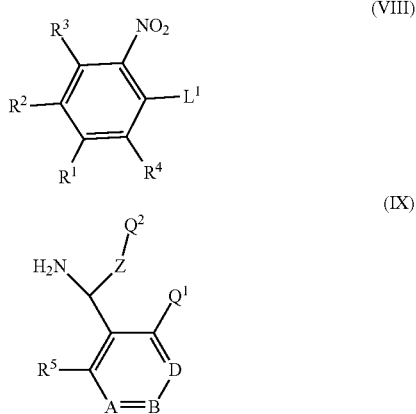

(VIII)

(IX)

wherein A, B, D, Z, $R^1$, $R^2$, $R^3$, $R^4$, $R^5$, $Q^1$ and $Q^2$ are as defined above, and $L^1$ represents a suitable leaving group.

The leaving group $L^1$ is suitably a halogen atom, for example fluorine or bromine.

The reaction is conveniently performed in the presence of a base, e.g. an inorganic base such as potassium carbonate, in a suitable solvent, e.g. an apolar solvent such as acetonitrile, at an elevated temperature.

The intermediates of formula (IX) may be prepared by a multi-step process starting from an intermediate of formula (X):

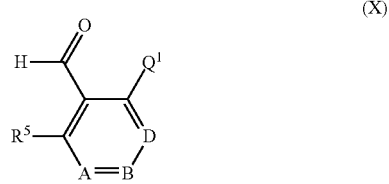

(X)

wherein A, B, D, $R^5$ and $Q^1$ are as defined above; which process comprises the following steps:

(i) reaction of intermediate (X) with (S)-tert-butylsulfinamide in the presence of $K_3PO_4/K_2HPO_4$ in a suitable solvent, e.g. tetrahydrofuran;

(ii) reacting the compound obtained from step (i) with a compound of formula $L^2$-Z-$Q^2$, wherein Z and $Q^2$ are as defined above and $L^2$ is a suitable leaving group, e.g. halogen, such as bromine, and activated zinc metal dust prepared according to conditions described by H. Hilpert et al. in *Journal of Medicinal Chemistry*, 2013, 56(10), 3980-3995, typically in the presence of a transition metal salt, e.g. copper(I) chloride, optionally at an elevated temperature; and (iii) reaction with a strong mineral acid, e.g. hydrochloric acid.

The intermediates of formula (X) wherein $R^5$ represents hydroxy may be transformed into the corresponding intermediate of formula (X) wherein $R^5$ represents difluoromethoxy by reaction with diethyl (bromodifluoromethyl) phosphonate at low temperature.

Alternatively, the intermediates of formula (X) wherein $R^5$ represents halogen, e.g. chloro, may be transformed into the corresponding intermediate of formula (X) wherein $R^5$ represents difluoromethoxy by a two-step process which comprises: (i) reaction with potassium hydroxide in water at low temperature; and (ii) reaction with diethyl (bromodifluoromethyl)phosphonate at low temperature.

The intermediates of formula (IV) wherein E represents a group of formula (Ea) as defined above, and $R^{12}$ represents hydrogen, may be prepared by a process which comprises the reduction, intramolecular cyclization and desulfination of an intermediate of formula (VIa):

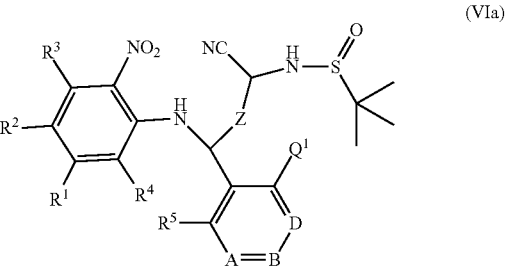

(VIa)

wherein A, B, D, Z, $R^1$, $R^2$, $R^3$, $R^4$, $R^5$ and $Q^1$ are as defined above.

The reaction is conveniently performed in the presence of tin(II) chloride, with the addition of a strong acid, e.g. hydrochloric acid, at an elevated temperature in a suitable solvent, e.g. ethanol.

Alternatively, the transformation may be effected by a procedure involving: (i) reduction using hydrogen gas under pressure, in the presence of zinc bromide and a hydrogenation catalyst, e.g. platinum on charcoal; and (ii) addition of a strong acid, e.g. hydrochloric acid, at an elevated temperature in a suitable solvent, e.g. ethanol.

The intermediates of formula (VIa) may be prepared by a multi-step process starting from an intermediate of formula (VIIa):

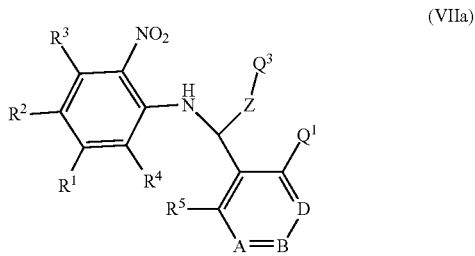

(VIIa)

wherein A, B, D, Z, R$^1$, R$^2$, R$^3$, R$^4$, R$^5$ and Q$^1$ are as defined above, and Q$^3$ represents —CH=CH$_2$; which process comprises the following steps:

(i) reacting intermediate (VIIa) with sodium periodate, in the presence of potassium dioxido(dioxo)osmium hydrate and a base, e.g. N,N-dimethylpyridinyl-4-amine or 2,6-dimethylpyridine, followed by addition of sodium thiosulfate, to afford the corresponding intermediate of formula (VIIa) wherein Q$^3$ represents —CH=O;

(ii) reacting the compound thereby obtained with (R)-2-methylpropane-2-sulfinamide in the presence of a transition metal catalyst, e.g. titanium(IV) isopropoxide, in a suitable solvent, e.g. dichloromethane, to afford the corresponding intermediate of formula (VIIa) wherein Q$^3$ represents —CH=N—S(=O)—C(CH$_3$)$_3$; and (iii) reacting the compound thereby obtained with sodium cyanide in the presence of scandium triflate in a suitable solvent, e.g. tetrahydrofuran.

The intermediates of formula (VIIa) as defined above may be prepared by reacting an intermediate of formula (VIII) as defined above with an intermediate of formula (IXa):

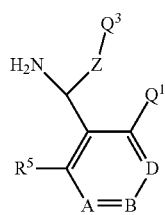

(IXa)

wherein A, B, D, Z, R$^5$, Q$^1$ and Q$^3$ are as defined above; under conditions analogous to those described above for the preparation of the intermediates of formula (VII).

The intermediates of formula (IXa) may be prepared from the intermediates of formula (X) by a process analogous to that described above for the preparation of the intermediates of formula (IX).

The intermediates of formula (V) wherein E represents a group of formula (Eb) or (Ec) as defined above, and R$^{12}$ represents hydrogen, may be prepared from an intermediate of formula (XI):

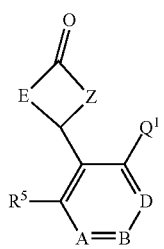

(XI)

wherein A, B, D, Z, E, R$^5$ and Q$^1$ are as defined above; by reduction of the carbonyl moiety according to methods known to the person skilled in the art.

The intermediates of formula (IV) wherein E represents a group of formula (Eb) or (Ec) as defined above, and R$^{12}$ represents methyl, may be prepared from an intermediate of formula (XI) utilising the following sequence of steps:

(i) reacting an intermediate of formula (XI) with 2-methylpropane-2-sulfinamide in the presence of titanium(IV) isopropoxide in a solvent, e.g. tetrahydrofuran;

(ii) adding a solution of methylmagnesium bromide, at low temperature, in a suitable solvent, e.g. dichloromethane; and (iii) removing the tert-butylsulphinyl moiety by treatment with a strong acid, e.g. hydrochloric acid, in a suitable solvent, e.g. 1,4-dioxane.

Alternatively, the intermediates of formula (IV) wherein E represents a group of formula (Eb) or (Ec) as defined above, and R$^{12}$ represents hydrogen, may be prepared from an intermediate of formula (XI) by reaction with a C$_{1-6}$ alkylsulfinamide, e.g. (R)-2-methylpropane-2-sulfinamide, in the presence of a transition metal catalyst, e.g. titanium(IV) ethoxide, in a suitable solvent, e.g. dichloromethane; followed by reduction with a suitable reducing agent, e.g. sodium borohydride, in a suitable solvent, e.g. tetrahydrofuran; and subsequent removal of the sulfinyl moiety, typically by treatment with a mineral acid, e.g. hydrochloric acid.

The intermediates of formula (XI) may be prepared by the intramolecular cyclization of an intermediate of formula (XII):

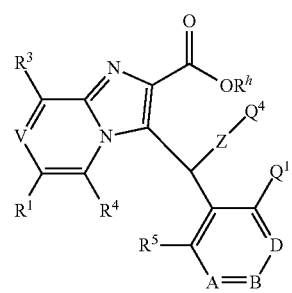

(XII)

wherein V is N or C—R$^2$, Q$^4$ is an electron-withdrawing group, preferably an ester moiety, and A, B, D, Z, R$^1$, R$^2$, R$^3$, R$^4$, R$^5$, R$^h$ and Q$^1$ are as defined above; in the presence of a base.

The reaction may conveniently be effected in a suitable solvent at an elevated temperature.

The intermediates of formula (XII) may be prepared by reacting an intermediate of formula (XIII) with an intermediate of formula (XIV):

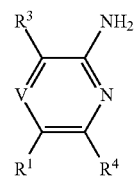

(XIII)

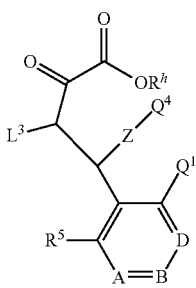

(XIV)

wherein A, B, D, V, Z, R¹, R³, R⁴, R⁵, Rʰ, Q¹ and Q⁴ are as defined above, and L³ represents a suitable leaving group.

The leaving group L³ is typically a halogen atom, e.g. bromo.

The reaction is conveniently effected at an elevated temperature in a suitable solvent, e.g. a $C_{1-4}$ alkanol such as ethanol, or an ether such as 1,4-dioxane or 1,2-dimethoxyethane, typically in the presence of magnesium sulphate.

Alternatively, the intermediates of formula (XII) wherein Z is methylene and Q⁴ is —CO₂H may be prepared by reacting an intermediate of formula (X) as defined above with an intermediate of formula (XV):

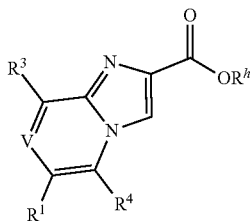

(XV)

wherein V, R¹, R³, R⁴ and Rʰ are as defined above; in the presence of Meldrum's acid, according to a method analogous to that described in WO 2009/156091; or by M. Kerr et al. in *J. Org. Chem.*, 2013, 78, 10534.

The reaction is conveniently effected at an elevated temperature in a suitable solvent, e.g. acetonitrile, in the presence of proline and magnesium sulphate.

In an alternative procedure, the compounds of formula (I) above, wherein R^f represents hydrogen and R⁸ is other than hydrogen, may be prepared by a process which comprises reacting a compound of formula R⁸—NH₂ with a compound of formula (XVI):

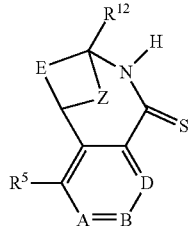

(XVI)

wherein A, B, D, Z, E, R⁵, R¹² and R^g are as defined above.

The reaction is conveniently performed at an elevated temperature in a suitable solvent, e.g. a cyclic ether such as tetrahydrofuran.

The intermediates of formula (XVI) above may be prepared by reacting a compound of formula (XVII):

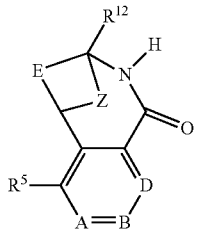

(XVII)

wherein A, B, D, Z, E, R⁵ and R¹² are as defined above; with 2,4-bis(4-methoxyphenyl)-1,3,2,4-dithiadiphosphetane-2,4-dithione (Lawesson's reagent).

The reaction is conveniently effected at an elevated temperature in a suitable organic solvent, e.g. a hydrocarbon solvent such as toluene.

The intermediates of formula (XVII) above may be prepared by the intramolecular cyclisation of a compound of formula (IV) as defined above in the presence of carbon monoxide and a transition metal catalyst.

The cyclization is generally effected at an elevated temperature under an elevated pressure of carbon monoxide. The reaction is conveniently carried out in a suitable solvent, e.g. 1,4-dioxane, dimethyl sulfoxide or N,N-dimethylacetamide.

Moreover, the cyclization will generally be performed in the presence of a base, e.g. an inorganic base such as sodium carbonate or potassium carbonate, and/or by activation using molecular sieves.

The transition metal catalyst of use in the above reaction is suitably selected from dichloro[1,3-bis(dicyclohexylphosphino)propane]palladium(II), dichloro[9,9-dimethyl-4,5-bis(diphenylphosphino)xanthene]palladium(II) and 2,2-dichloro-1,1,3,3-tetra-cyclohexyl-1λ⁵,3λ⁵-palladocyclohexane. Alternatively, a solution of palladium (II) acetate and 4,5-bis(diphenylphosphino)-9,9-dimethylxanthene (Xantphos) in a suitable solvent may be used.

In a variant procedure, the reaction may be performed using molybdenum hexacarbonyl as an alternative source of carbon monoxide.

Where they are not commercially available, the starting materials of formula (VIII), (X), (XIII), (XIV) and (XV) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art.

By way of example, a compound which contains a hydroxy group may be alkylated by treatment with the appropriate alkyl halide in the presence of a base, e.g. sodium hydride, or silver oxide.

A compound which contains hydroxy may be converted into the corresponding fluoro-substituted compound by treatment with diethylaminosulfur trifluoride (DAST) or bis(2-methoxyethyl)aminosulfur trifluoride (BAST). A compound which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound which contains an N—H moiety may be alkylated by treatment with the appropriate alkyl halide, typically at an elevated temperature in an organic solvent such as acetonitrile; or at ambient temperature in the presence of a base, e.g. potassium hydroxide, in a suitable solvent, e.g. tetrahydrofuran, in the presence of tetrabutylammonium bromide; or at an elevated temperature in the presence of a base, e.g. sodium hydride, with or without tetrabutylammonium iodate, in a suitable solvent, e.g. tetrahydrofuran; or at elevated temperature in the presence of an alkali metal carbonate such as potassium carbonate or cesium carbonate, in a suitable solvent, e.g. a dipolar aprotic solvent such as N,N-dimethylformamide. A compound which contains an N—H moiety may be methylated by treatment with formaldehyde in the presence of a reducing agent, e.g. sodium triacetoxyborohydride.

A compound which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound which contains an N—H moiety may be converted into the corresponding compound wherein the nitrogen atom is substituted by $C_{1-6}$ alkoxycarbonyl, e.g. methoxycarbonyl, by treatment with the corresponding $C_{1-6}$ alkoxycarbonyl halide in the presence of a base, e.g. potassium carbonate, in a suitable solvent, e.g. N,N-dimethylformamide.

A compound substituted by amino (—NH$_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl) amino, by treatment with the appropriate $C_{1-6}$ alkylsulphonyl halide, e.g. a $C_{1-6}$ alkylsulphonyl chloride such as methanesulphonyl chloride, in the presence of a suitable base, e.g. N,N-diisopropylethylamine, in a suitable solvent, e.g. dichloromethane.

Thus, a compound substituted by amino may be transformed into the corresponding compound substituted by —NHSO$_2$R$^e$ by treatment with a compound of formula R$^e$—SO$_2$Cl.

Similarly, a compound substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound containing the moiety —S— may be converted into the corresponding compound containing the moiety —S(O)— by treatment with 3-chloroperoxybenzoic acid. Likewise, a compound containing the moiety —S(O)— may be converted into the corresponding compound containing the moiety —S(O)$_{2-6}$ by treatment with 3-chloroperoxybenzoic acid. Alternatively, a compound of formula (I) containing the moiety —S— may be converted into the corresponding compound containing the moiety —S(O)$_{2-6}$ by treatment with Oxone® (potassium peroxymonosulfate).

A compound containing an aromatic nitrogen atom may be converted into the corresponding N-oxide derivative by treatment with 3-chloroperoxybenzoic acid.

A compound which contains a carbonyl (C═O) moiety may be converted into the corresponding compound containing a CH(OH) functionality by treatment with a suitable borohydride reagent, e.g. lithium tri-sec-butyl borohydride or sodium borohydride, in a suitable solvent e.g. tetrahydrofuran.

A compound wherein R$^1$ represents halogen, e.g. chloro or bromo, may be converted into the corresponding compound wherein R$^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected at an elevated temperature in the presence of a transition metal catalyst, e.g. [1,1'-bis(diphenyl-phosphino) ferrocene]dichloropalladium(II), tetrakis(triphenylphosphine)palladium(0), bis[3-(diphenylphosphanyl)cyclopenta-2,4-dien-1-yl]iron-dichloropalladium-dichloromethane complex, or tris(dibenzylideneacetone)dipalladium(0) and tricyclohexyl-phosphonium tetrafluoroborate, or (2-dicyclohexylphosphino-2',4',6'-triisopropyl-1,1'-biphenyl)[2-(2-aminoethyl)phenyl]palladium(II) chloride (XPhos Pd G1), and a base, e.g. an inorganic base such as sodium carbonate, potassium carbonate or cesium carbonate, or potassium phosphate, in a suitable organic solvent, e.g. 1,4-dioxane or n-butanol, and optionally water.

A compound wherein R$^1$ represents 2-oxo-(1H)-pyridinyl may be obtained by treatment of the corresponding compound wherein R$^1$ represents 2-methoxypyridinyl with pyridine hydrochloride at an elevated temperature.

A compound wherein R$^1$ represents an ester moiety may be obtained by reacting the corresponding compound wherein R$^1$ is halogen, e.g. chloro, with a base, e.g. sodium carbonate, and the appropriate alcohol in the presence of carbon monoxide and a transition metal catalyst, typically [1,3-bis(dicyclohexylphosphino)propane]palladium(II).

A compound wherein R$^1$ represents cyano may be obtained by reacting the corresponding compound wherein R$^1$ is halogen, e.g. chloro, with zinc cyanide in the presence of a transition metal catalyst, e.g. tetrakis(triphenylphosphine)palladium(0), in a suitable solvent, e.g. N,N-dimethylformamide.

In general, a compound containing a —C═C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound containing an ester moiety, e.g. a $C_{2-6}$ alkoxycarbonyl group such as methoxycarbonyl or ethoxycarbonyl, may be converted into the corresponding compound containing a carboxy (—CO$_2$H) moiety by treatment with an acid, e.g. a mineral acid such as hydrochloric acid.

A compound containing an ester moiety, e.g. a $C_{2-6}$ alkoxycarbonyl group such as methoxycarbonyl or ethoxycarbonyl, may alternatively be converted into the corresponding compound containing a carboxy (—CO$_2$H) moiety by treatment with a base, e.g. an alkali metal hydroxide selected from lithium hydroxide, sodium hydroxide and potassium hydroxide; or an organic base such as sodium methoxide or sodium ethoxide.

A compound containing a carboxy (—CO$_2$H) moiety may be converted into the corresponding compound containing an amide moiety by treatment with the appropriate amine in the presence of a condensing agent such as 1-ethyl-3-(3-dimethylaminopropyl)-carbodiimide.

A compound containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound containing a carbonyl (C═O) moiety may be converted into the corresponding compound containing a —C(CH$_3$)(OH)— moiety by treatment with methylmagnesium bromide. Similarly, a compound containing a carbonyl (C=O) moiety may be converted into the corresponding compound containing a —C(CF$_3$)(OH)— moiety by treatment with (trifluoromethyl)trimethylsilane and cesium fluoride. A compound containing a carbonyl (C=O) moiety may be converted into the corresponding compound containing a —C(CH$_2$NO$_2$)OH)— moiety by treatment with nitromethane.

A compound containing a hydroxymethyl moiety may be converted into the corresponding compound containing a formyl (—CHO) moiety by treatment with an oxidising agent such as Dess-Martin periodinane. A compound containing a hydroxymethyl moiety may be converted into the corresponding compound containing a carboxy moiety by treatment with an oxidising agent such as tetrapropylammonium perruthenate.

A compound containing an aryl or heteroaryl moiety may be transformed into the corresponding compound, wherein a hydrogen atom in the aryl or heteroaryl moiety has been replaced by chloro or bromo, by reaction with N-chlorosuccinimide or N-bromo-succinimide respectively in a suitable solvent, e.g. N,N-dimethylformamide, according to methods known to the person skilled in the art.

A compound containing an aryl moiety bearing a difluoromethoxy group may be transformed into the corresponding compound, wherein the difluoromethoxy group in the aryl moiety has been replaced by a hydroxy group, by reaction with sodium bis(trimethyl-silyl)amide (NaHMDS) in a suitable solvent, e.g. tetrahydrofuran.

A compound containing an aryl or heteroaryl moiety may be transformed into the corresponding compound, wherein a hydrogen atom in the aryl or heteroaryl moiety has been replaced by trifluoromethyl, by a stepwise procedure which comprises: (i) treatment with trifluoroacetic acid in a suitable solvent, e.g. acetonitrile; and (ii) addition of trifluoromethanesulphonyl chloride, followed by [4,4'-bis(tert-butyl)-2,2'-bipyridine]bis-{3,5-difluoro-2-[5-(trifluoromethyl)pyridin-2-yl]phenyl}iridium(III) hexafluorophosphate, according to conditions analogous to those described by McMillan et al. in *Nature*, 2011, 480, 224.

A compound substituted by phosphate(C$_{1-6}$)alkyl may be prepared from the corresponding compound substituted by hydroxy(C$_{1-6}$)alkyl by a stepwise procedure which comprises: (i) treatment with dibenzyl N,N-diisopropylphosphoramidite in a suitable solvent, e.g. dichloromethane, followed by treatment with hydrogen peroxide; and (ii) hydrogenolysis, e.g. using hydrogen gas under pressure, in the presence of a suitable catalyst, e.g. palladium on charcoal, according to a method analogous to those described by S. P. Green et al. in *Organic Process Research & Development*, 2002, 6, 109-112. A compound substituted by a salt of phosphate(C$_{1-6}$)alkyl may be prepared by performing step (ii) in the presence of a suitable alkali metal base or alkaline earth metal base.

Similarly, an isolated compound substituted by phosphate (C$_{1-6}$)alkyl may be converted into the corresponding compound substituted by a salt of phosphate(C$_{1-6}$)alkyl by treatment with an appropriate base, e.g. an alkali metal base, or an alkaline earth metal base, or ammonia, or an organic amine, in a suitable solvent according to methods known to the person skilled in the art. Suitable alkali metal bases include sodium hydroxide and potassium hydroxide. Suitable alkaline earth metal bases include calcium hydroxide. Suitable organic amines include triethylamine.

A compound substituted by (C$_{1-6}$)alkylphosphate(C$_{1-6}$) alkyl may be prepared from the corresponding compound substituted by hydroxy(C$_{1-6}$)alkyl by a stepwise procedure which comprises: (i) reacting cyanoethyl phosphoramidite with the appropriate C$_{1-6}$ alkanol in the presence of a base, e.g. N,N-diisopropylethylamine, in a suitable solvent, e.g. dichloromethane; (ii) addition of the relevant compound substituted by hydroxy-(C$_{1-6}$)alkyl in a suitable solvent, e.g. dichloromethane; and (iii) oxidation and subsequent treatment with a suitable base, according to a method analogous to those described by Nam, N—H. et al. in *Bio-org. Med. Chem.*, 2004, 12, 6255; and in WO 2012/177707.

A compound substituted by sulphate(C$_{1-6}$)alkyl may be prepared by treatment of the corresponding compound substituted by hydroxy(C$_{1-6}$)alkyl with pyridine:sulphur trioxide complex, according to a method analogous to that described by E. Lacko et al. in *Current Medicinal Chemistry*, 2012, 19, 4699; or by treatment with chlorosulphonic acid in the presence of triethylamine, according to a method analogous to that described in WO 2004/087720.

A compound substituted by phosphate-methoxy(C$_{1-6}$) alkyl may be prepared by reacting the corresponding compound substituted by hydroxy(C$_{1-6}$)alkyl with a suitable base, e.g. sodium hydride, in a suitable solvent, e.g. 1,2-dimethoxyethane, followed by addition of chloromethyl di-tert-butylphosphate, with subsequent dealkylation at an elevated temperature, according to a method analogous to that described in WO 2012/135082.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non-desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

Compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (the skilled person will appreciate that a lower $IC_{50}$ figure denotes a more active compound).

Certain compounds in accordance with the present invention potently inhibit the binding of a fluorescence conjugate to TNFα when tested in the fluorescence polarisation assay described herein. Indeed, when tested in that assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (as before, the skilled person will appreciate that a lower $IC_{50}$ figure denotes a more active compound).

The compounds of the Examples have been tested in one or both of the assays described below.

Fluorescence Polarisation Assay
Preparation of Compound (A)
1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—can be prepared by the procedure described in Example 499 of WO 2013/186229; or by a procedure analogous thereto.

Preparation of Fluorescence Conjugate
Compound (A) (27.02 mg, 0.0538 mmol) was dissolved in DMSO (2 mL). 5 (-6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα
Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An $IC_{50}$ value was calculated using XLfit™ (4 parameter logistic model) in ActivityBase.

When tested in the fluorescence polarisation assay, compounds of the accompanying Examples were found to exhibit $IC_{50}$ values of 50 μM or better.

When tested in the fluorescence polarisation assay, compounds of the accompanying Examples exhibit $IC_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, ideally in the range of about 0.01 nM to about 500 nM, appositely in the range of about 0.01 nM to about 100 nM, and preferably in the range of about 0.01 nM to about 25 nM.

Reporter Gene Assay
Inhibition of TNFα-Induced NF-κB Activation
Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFN minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, the compounds of the accompanying Examples were all found to exhibit $IC_{50}$ values of 50 μM or better.

When tested in the reporter gene assay, compounds of the accompanying Examples exhibit $IC_{50}$ values generally in the range of about 0.01 nM to about 50 μM, usually in the range of about 0.01 nM to about 20 μM, typically in the range of about 0.01 nM to about 5 μM, suitably in the range of about 0.01 nM to about 1 μM, appositely in the range of about 0.01 nM to about 500 nM, ideally in the range of about 0.01 nM to about 100 nM, and preferably in the range of about 0.01 nM to about 25 nM.

The following Examples illustrate the preparation of compounds according to the invention.

EXAMPLES

Abbreviations

DCM: dichloromethane EtOAc: ethyl acetate
DMF: N,N-dimethylformamide MeOH: methanol
DMSO: dimethyl sulfoxide THF: tetrahydrofuran
EtOH: ethanol DEA: diethanolamine
DIBAL-H: diisobutylaluminium hydride TFA: trifluoroacetic acid
DIAD: diisopropyl (E)-1,2-diazenedicarboxylate
Lawesson's reagent: 2,4-bis(4-methoxyphenyl)-1,3,2,4-dithiadiphosphetane-2,3-dithione XPhos Pd G1: (2-dicyclohexylphosphino-2',4',6'-triisopropyl-1,1'-biphenyl)[2-(2-aminoethyl) phenyl]palladium(II) chloride
h: hour r.t.: room temperature
M: mass RT: retention time
HPLC: High Performance Liquid Chromatography
LCMS: Liquid Chromatography Mass Spectrometry
ES+: Electrospray Positive Ionisation All NMR spectra were obtained either at 300 MHz or at 400 MHz.

All reactions involving air- or moisture-sensitive reagents were performed under a nitrogen atmosphere using dried solvents and glassware.

LCMS Data Determination
Method 1 (LCMS Basic)
A QDA Waters simple quadrupole mass spectrometer is used for LC-MS analysis.
This spectrometer is equipped with an ESI source and an UPLC Acquity Classic with diode array detector (210 to 400 nm).
Data are acquired in a full MS scan from m/z 50 to 1000 in positive mode with an acidic elution.
The reverse phase separation is carried out at 45° C. on a Waters Acquity UPLC BEH C18 1.7 µm (2.1×50 mm) column for basic elution.
Gradient Elution is Performed with:
H$_2$O/acetonitrile/ammonium formate (95/5/63 mg/L)+50 µL NH$_4$OH (solvent A)
Acetonitrile/H$_2$O/ammonium formate (95/5/63 mg/L)+50 µL NH$_4$OH (solvent B)
Gradient Program:
HPLC flow rate: 0.4 mL/minute to 0.5 mL/minute
Injection volume: 1 µL
Full flow in MS.

| Time (min) | A (%) | B (%) | Flow (mL/min) |
| --- | --- | --- | --- |
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |
| 4.1 | 99 | 1 | 0.4 |
| 4.8 | 90 | 1 | 0.4 |

Method 2
Method Name S
Instrument Agilent 6890N; Column: RXi-SMS 20 m, ID 180 µm, df 0.8 µm
Average velocity 50 cm/s; carrier gas: He
Initial temperature 60° C.; initial time: 1.5 minutes; solvent delay: 1.3 minutes
Rate 50° C./minute; final temperature: 250° C.; final time 3.7 minutes
Split ratio 20:1; injector temperature: 250° C.; injection volume 1 µL
Detection MSD (EI—positive); detection temp.: 280° C.; mass range 50-550
Detection FID; detector temperature: 300° C.
Method 3
Column: X-Bridge C18 Waters 2.1×20 mm, 2.5 m column
Mobile Phase A: 10 mM ammonium formate in water+0.1% ammonia solution
Mobile Phase B: acetonitrile+5% water+0.1% ammonia solution
Gradient program: Flow rate 1 mL/min

| Time | A % | B % |
| --- | --- | --- |
| 0.00 | 96.00 | 4.00 |
| 1.50 | 5.00 | 95.00 |
| 2.25 | 5.00 | 95.00 |
| 2.50 | 96.00 | 4.00 |

Method 4 (LCMS Acidic)
A QDA Waters simple quadrupole mass spectrometer is used for LC-MS analysis.
This spectrometer is equipped with an ESI source and an UPLC Acquity Hclass with diode array detector (210 to 400 nm).
Data are acquired in a full MS scan from m/z 50 to 1000 in positive mode with an acidic elution.
The reverse phase separation is carried out at 45° C. on a Waters Acquity UPLC HSS T3 1.8 µm (2.1×50 mm) column for acidic elution.
Gradient Elution is Performed with:
Water (solvent A)
Acetonitrile (solvent B)
Water/acetonitrile/formic acid 0.5% (solvent C)
Gradient Program:
HPLC flow rate: 0.6 mL/minute to 0.7 mL/minute
Injection volume: 1 µL
Full flow in MS.

| Time (min) | A (%) | B (%) | C (%) | Flow (mL/min) |
| --- | --- | --- | --- | --- |
| 0 | 90 | 0 | 10 | 0.6 |
| 0.3 | 90 | 0 | 10 | 0.6 |
| 3.2 | 0 | 90 | 10 | 0.6 |
| 3.25 | 0 | 90 | 10 | 0.7 |
| 4 | 0 | 90 | 10 | 0.7 |
| 4.1 | 90 | 0 | 10 | 0.6 |
| 5.4 | 90 | 0 | 10 | 0.6 |

It will be apparent to the person skilled in the art that different retention times (RT) may be obtained for LCMS if different analytical conditions are used.
Method 5
Column: X-Bridge C18 Waters 2.1×20 mm, 2.5 µm column
Mobile Phase A: 10 mM ammonium formate in water+0.1% ammonia solution
Mobile Phase B: acetonitrile+5% water+0.1% ammonia solution
Gradient program: Flow rate pump 1: 1 mL/min; Flow rate pump 2: 0.5 mL/min

| Pump 1: | | | Pump 2: | | |
|---|---|---|---|---|---|
| Time | A % | B % | Time | A % | B % |
| 0.00 | 95.10 | 4.90 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.10 | 4.90 | | | |

Method 6
Column: X-Bridge C18 Waters 2.1×20 mm, 2.5 μm column
Mobile Phase A: 10 mM ammonium formate in water+0.1% formic acid
Mobile Phase B: acetonitrile+5% water+0.1% formic acid
Gradient program: Flow rate pump 1: 1 mL/min; Flow rate pump 2: 0.5 mL/min

| Pump 1: | | | Pump 2: | | |
|---|---|---|---|---|---|
| Time | A % | B % | Time | A % | B % |
| 0.00 | 95.00 | 5.00 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.00 | 5.00 | | | |

Preparative HPLC-MS
Method 1 (Acidic Preparative LCMS)
Waters Fraction-Lynx system, with 2545 pump, 2998 PDA, 2767 fraction collector and a Waters 3100 MS.
pH3_35_50 focused gradient, reverse phase.
Waters XBridge Prep C18 OBD column, 19×100 mm, 5 μm.
Solvent A: 10 mM ammonium bicarbonate+0.1% formic acid
Solvent B: acetonitrile+0.1% formic acid

| Time (min) | % A | % B |
|---|---|---|
| 0 | 90 | 10 |
| 2.3 | 65 | 35 |
| 11 | 50 | 50 |
| 11.5 | 5 | 95 |
| 13 | 5 | 95 |
| 13.2 | 90 | 10 |

Flow rate: 19 mL/minute (+1 mL/minute acetonitrile ACD)
Column temperature: ambient
Method 2 (Basic Preparative LCMS)
Waters Fraction-Lynx system, with 2545 pump, 2998 PDA, 2767 fraction collector and a
Waters 3100 MS.
pH10_35_30 focused gradient, reverse phase.
Waters XBridge Prep C18 OBD column, 19×100 mm, 5 μm.
Solvent A: 10 mM ammonium bicarbonate+0.1% NH$_4$OH
Solvent B: acetonitrile+0.1% NH$_4$OH

| Time (min) | % A | % B |
|---|---|---|
| 0 | 90 | 10 |
| 2.3 | 65 | 35 |
| 11 | 50 | 50 |
| 11.5 | 5 | 95 |
| 13 | 5 | 95 |
| 13.2 | 90 | 10 |

Flow rate: 19 mL/minute (+1 mL/minute acetonitrile ACD)
Column temperature: ambient Method 3
pH 10 25_40 gradient, reverse phase
Column: XBridge Prep Phenyl, 5 μm OBD, 19×150 mm
Mobile Phase A: 10 mM ammonium bicarbonate in water+0.1% ammonia solution
Mobile Phase B: acetonitrile+5% water+0.1% ammonia solution

| Time (min) | A % | B % |
|---|---|---|
| 0.00 | 75.00 | 25.00 |
| 2.50 | 75.00 | 25.00 |
| 11.00 | 60.00 | 40.00 |
| 11.50 | 5.00 | 95.00 |
| 13.00 | 75.00 | 25.00 |

Flow rate: 19 mL/minute

Intermediate 1

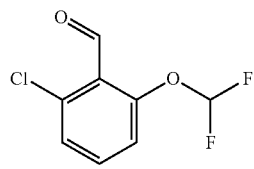 [SMILES: O=Cc1c(Cl)cccc1OC(F)F]

2-Chloro-6-(difluoromethoxy)benzaldehyde

To 2-chloro-6-hydroxybenzaldehyde (20 g, 128.2 mmol) in acetonitrile (150 mL) was added a solution of potassium hydroxide (71.7 g, 1282 mmol) in water (50 mL) at 0° C. The reaction mixture was stirred at 0° C. for 10 minutes, then diethyl (bromo-difluoromethyl)phosphonate (36.4 mL, 205.1 mmol) was added at 0° C. The reaction mixture was stirred at 0° C. for 30 minutes, then poured into water (500 mL). The aqueous layer was extracted with EtOAc (2×1 L). The organic layer was washed with water (500 mL) and brine (500 mL), then dried over anhydrous sodium sulphate and filtered. The organic layers were evaporated under reduced pressure. The resulting crude residue was purified by column chromatography (SiO$_2$, 5% EtOAc in hexane) yielding the title compound (13.9 g, 53%) as a yellow oil. $\delta_H$ (400 MHz, CDCl$_3$) 10.46 (s, 1H), 7.49 (t, J 8.2 Hz, 1H), 7.37 (dd, J 8.1, 1.1 Hz, 1H), 7.20 (m, 1H), 6.61 (t, 1H).

Intermediate 2

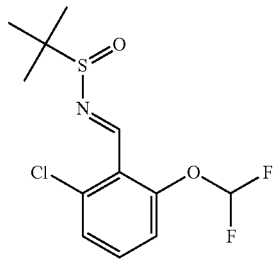 [SMILES: CC(C)(C)S(=O)/N=C/c1c(Cl)cccc1OC(F)F]

N-{[2-Chloro-6-(difluoromethoxy)phenyl]methylene}-(S)-2-methylpropane-2-sulfinamide To a solution of Intermediate 1 (20 g, 97.08 mmol) in dry THF (100 mL) at 0° C. were added (S)-(−)-tert-butylsulfinamide (12.92 g, 106.79 mmol), K₃PO₄ (61.73 g, 291.2 mmol) and K₂HPO₄ (50.6 g, 291.2 mmol). The reaction mixture was stirred at r.t. for 18 h, then filtered through celite and washed with EtOAc (1 L). The organic layer was washed with water (500 mL) and brine (500 mL), then dried over anhydrous sodium sulphate. The organic layer was filtered and evaporated under reduced pressure, then the residue was purified by column chromatography (SiO₂, 10% EtOAc in hexane), to afford the title compound (20 g, 87%) as a yellow oil. $\delta_H$ (400 MHz, CDCl₃) 8.90 (s, 1H), 7.45-7.32 (m, 2H), 7.29-7.15 (m, 1H), 6.82-6.34 (m, 1H), 1.29 (s, 9H). LCMS (ES+) 309.90 (M+H)⁺, RT 2.73 minutes.

Intermediate 3

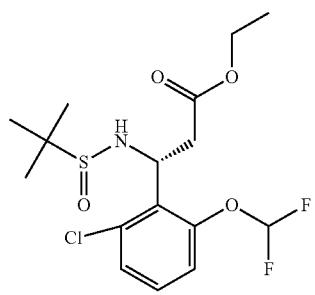 [SMILES: CCOC(=O)C[C@@H](NS(=O)C(C)(C)C)c1c(Cl)cccc1OC(F)F]

Ethyl (3R)-3-{[(S)-tert-butylsulfinyl]amino}-3-[2-chloro-6-(difluoromethoxy)phenyl]-propanoate Zinc powder (150 g) was taken up in 1N HCl (500 mL), stirred for 10 minutes and decanted. The zinc dust powder was washed with water (3×500 mL) and decanted. The powder was further washed with acetone (3×500 mL), decanted and dried under vacuum. To the resulting activated zinc dust (105 g, 1618 mmol) in dry THF (150 mL) was added CuCl (19.2 g, 194 mmol) and the reaction mixture was heated under reflux for 30 minutes. The reaction mixture was cooled to room temperature and ethyl bromoacetate (45 mL, 404 mmol) in THF (100 mL) was added dropwise. The reaction mixture was stirred at 50° C. for 30 minutes. The reaction mixture was cooled to 0° C. and Intermediate 2 (50 g, 161 mmol) in THF (100 mL) was added. The reaction mixture was warmed to r.t. and stirred for 3 h, then filtered through celite and washed with EtOAc (700 mL). The organic layer was washed with 1N citric acid (500 mL), saturated aqueous sodium bicarbonate solution (500 mL), water (500 mL) and brine (500 mL). The organic layers were separated and dried over anhydrous sodium sulphate, then filtered and evaporated under reduced pressure. The residue was purified by chromatography (SiO₂, 40% EtOAc in hexane) to afford the title compound (59 g, 92%) as a yellow oil. $\delta_H$ (400 MHz, CDCl₃) 7.29-7.21 (m, 2H), 7.05 (d, J 7.3 Hz, 1H), 6.82-6.34 (m, 1H), 5.59 (m, 1H), 4.36 (s, 1H), 4.18-4.02 (m, 2H), 3.25 (dd, J 15.6, 7.5 Hz, 1H), 3.01 (dd, J 15.3, 7.5 Hz, 1H), 1.31-1.11 (m, 12H).

Intermediate 4

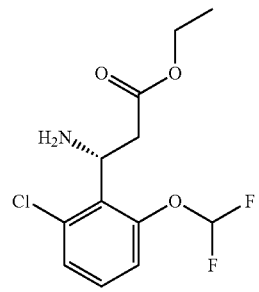 [SMILES: CCOC(=O)C[C@@H](N)c1c(Cl)cccc1OC(F)F]

Ethyl (3R)-3-amino-3-[2-chloro-6-(difluoromethoxy)phenyl]propanoate hydrochloride To a solution of Intermediate 3 (32 g, 80.6 mmol) in a diethyl ether:ethanol mixture (2:1, 75 mL) was added 4M HCl in 1,4-dioxane (70 mL). The reaction mixture was stirred at r.t. for 1 h, then concentrated under reduced pressure. The residue was triturated with diethyl ether (500 mL) to afford the title compound (22 g, 93%) as a yellow solid. $\delta_H$ (400 MHz, CDCl₃) 8.93 (d, J 6.2 Hz, 2H), 7.32-7.10 (m, 3H), 6.96 (s, 1H), 5.42 (m, 1H), 4.08 (q, J 7.0 Hz, 2H), 3.36 (dd, J 16.5, 7.0 Hz, 1H), 3.14 (dd, J 16.5, 7.8 Hz, 1H), 1.34 (t, J 7.1 Hz, 3H).

Preparative Intermediate 5

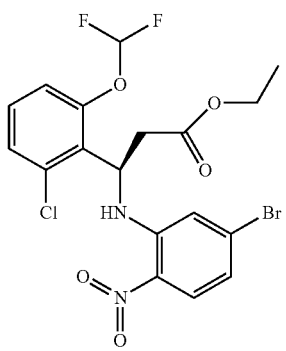 [SMILES: CCOC(=O)C[C@@H](Nc1cc(Br)ccc1[N+](=O)[O-])c1c(Cl)cccc1OC(F)F]

Ethyl (3R)-3-(5-bromo-2-nitroanilino)-3-[2-chloro-6-(difluoromethoxy)phenyl]-propanoate To a solution of Intermediate 4 (9.3 g, 28.3 mmol) in acetonitrile (80 mL) were added potassium carbonate (11.73 g, 84.9 mmol) and 4-bromo-2-fluoro-1-nitrobenzene (7.4 g, 34 mmol). The reaction mixture was stirred at 80° C. overnight, then diluted with EtOAc (150 mL) and washed with water (150 mL). The organic layer was separated and dried over anhydrous sodium sulphate, then filtered and concentrated under reduced pressure. The residue was purified by chromatography (SiO₂, 10% EtOAc in hexane) to afford the title compound (12.5 g, 90%) as a yellow oil. LCMS Method 1 (ES+) 493 (M+H)⁺.

Preparative Intermediate 6

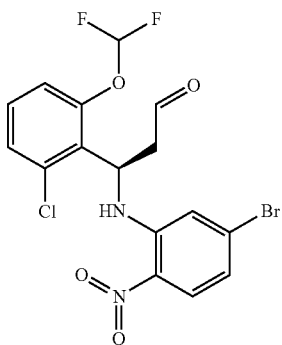 [SMILES: O=CC[C@@H](Nc1cc(Br)ccc1[N+](=O)[O-])c1c(Cl)cccc1OC(F)F]

(3R)-3-(5-Bromo-2-nitroanilino)-3-[2-chloro-6-(difluoromethoxy)phenyl]propanal

To a solution of Intermediate 5 (12.5 g, 25.4 mmol) in THF (130 mL) at −78° C. was added DIBAL-H (50.8 mL, 50.8 mmol) dropwise. The reaction mixture was stirred for 2 h at −78° C., then quenched with aqueous ammonium chloride solution. The reaction mixture was diluted with EtOAc and filtered through celite. The filtrate was washed with water. The organic layer was separated and dried over sodium sulphate, then filtered and evaporated under reduced pressure. The crude material was purified by chromatography (SiO$_2$, 15% EtOAc in hexane) to give the title compound (9.0 g, 80%) as a yellow oil. δ$_H$ (400 MHz, CDCl$_3$) 9.80 (d, J 1.3 Hz, 1H), 8.78 (d, J 9.0 Hz, 1H), 7.99 (d, J 9.0 Hz, 1H), 7.27 (d, J 3.2 Hz, 2H), 7.21-7.08 (m, 1H), 6.81-6.66 (m, 2H), 5.93 (m, 1H), 3.56-3.38 (m, 2H), 3.12 (dd, J 17.9, 5.2 Hz, 1H).

Preparative Intermediate 7

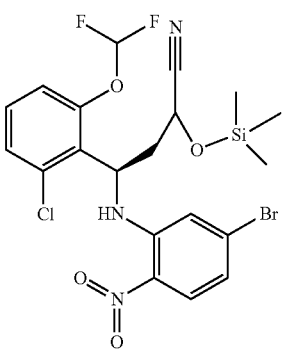 [SMILES: C[Si](C)(C)OC(C#N)C[C@@H](Nc1cc(Br)ccc1[N+](=O)[O-])c1c(Cl)cccc1OC(F)F]

(4R)-4-(5-Bromo-2-nitroanilin)-4-[2-chloro-6-(difluoomethoxy)phenyl]-2-(trimethyl-silyloxy)butanenitrile To a solution of Intermediate 6 (9.0 g, 20 mmol) in DCM (150 mL) were added ZnI$_2$ (0.64 g, 2 mmol), triethylamine (0.28 mL, 2 mmol) and trimethylsilyl cyanide (5.0 mL, 40 mmol). The reaction mixture stirred at r.t. for 2 h, then water (200 mL) was added and the mixture was extracted with DCM (500 mL). After evaporation of the organic layer, the title compound (9.0 g, crude material) was obtained as a yellow oil, which was utilised without additional purification.

Preparative Intermediate 8

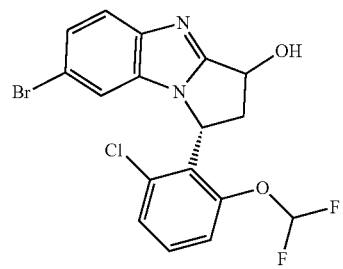 [SMILES: OC1C[C@H](c2c(Cl)cccc2OC(F)F)n2c1nc1ccc(Br)cc12]

(1R)-7-Bromo-1-[2-chloro-6-(difluoromethoxy)phenyl]-2,3-dihydro-1H-pyrrolo[1,2-a]-benzimidazol-3-ol To a solution of Intermediate 7 (9 g, 16.4 mmol) in EtOH (150 mL) was added SnCl$_2$ (15.6 g, 82 mmol). The reaction mixture was heated at 80° C. for 2 h, then quenched with water and basified to pH 8 using 1N KOH. The reaction mixture was diluted with EtOAc and filtered through celite. The organic layer was washed with water and brine, then dried over anhydrous sodium sulphate, filtered and concentrated under reduced pressure. The residue was purified by chromatography (SiO$_2$, 60% EtOAc in hexane), then triturated with hexane:EtOAc, to yield the title compound (3.0 g, 43%) as a yellow solid. LCMS Method 1 (ES+) 431 (Br$^{81}$/Cl$^{35}$ and/or Br$^{79}$/Cl$^{37}$) (M+H)$^+$.

Preparative Intermediates 9 & 10

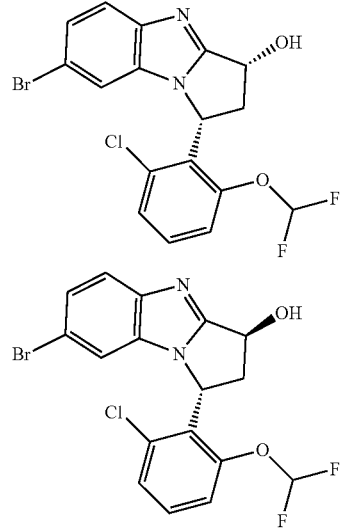

Intermediate 9

(1R,3R)-7-Bromo-1-[2-chloro-6-(difluoromethoxy)phenyl]-23-dihydro-1H-pyrrolo[1,2-a]benzimidazol-3-ol

Intermediate 10

(1R,3S)-7-Bromo-1-[2-chloro-6-(difluoromethoxy)phenyl]-2,3-dihydro-1H-pyrrolo[1,2-a]benzimidazol-3-ol Intermediate 8 (12.5 g) was subjected to preparative SFC chromatography under the following conditions: Chiracel OD column (column size: 50×266 mm, flow: 360 mL/minute, injection: 20 mg, frequency: 4 minutes, 25° C., $CO_2$+20% MeOH).

The peaks thus separated were analysed under the following analytical conditions: Chiralcel OD-H (column size: 250×4.6 mm, flow 1 mL/minute at 30° C. using 100% methanol containing 0.1% DEA).

Intermediate 9 (3.63 g, 29%) was isolated as the third-eluting diastereomer (RT 5.4 minutes). $\delta_H$ (400 MHz, DMSO-$d_6$) 7.57 (m, 2.3H), 7.45 (m, 0.8H), 7.35 (d, J 8.0 Hz, 0.6H), 7.26 (m, 1H), 7.17 (m, 0.3H), 6.83 (t, J 72.5 Hz, 1H), 6.69 (br s, 1H), 6.15 (m, 1H), 6.07 (m, 1H), 5.38 (m, 1H), 3.38 (m, 1H), 2.67 (m, 1H) as a 7:3 mixture of rotamers. LCMS acidic (ES+) 429.1/431.1/433.1 (M+H)$^+$, RT 4.31 minutes.

The second-eluting diastereomers (RT 4.7 minutes) were collected and subjected to preparative SFC chromatography under the following conditions: Whelko 01 (R,R) column (column size: 50×227 mm, flow: 360 mL/minute, injection: 690 mg, frequency: 5.5 minutes, 25° C., $CO_2$+20% EtOH).

The peaks thus separated were analysed under the following analytical conditions: Chiralcel OD-H (column size: 250×4.6 mm, flow: 1 mL/minute at 30° C. using 50:50 heptane/isopropyl alcohol containing 0.1% DEA).

The second eluting diastereomer (RT 5.9 minutes) gave Intermediate 10 (4.46 g, 36%), after evaporation of the combined fractions. $\delta_H$ (400 MHz, DMSO-$d_6$) 7.55 (m, 3.4H), 7.31 (m, 1.4H), 7.12 (d, J 7.8 Hz, 0.6H), 7.03 (t, J 73.0 Hz, 0.6H), 6.89 (s, 0.6H), 6.81 (s, 0.4H), 6.32 (dd, J 8.4, 5.9 Hz, 1H), 6.10 (d, J 6.6 Hz, 1H), 5.32 (m, 0.6H), 5.26 (t, J 6.9 Hz, 0.4H), 3.13 (m, 1H), 2.93 (m, 1H) as a 6:4 mixture of rotamers. LCMS acidic (ES+) 429.1/431.1/433.1 (M+H)$^+$, RT 4.40 minutes.

Preparative Intermediate 10

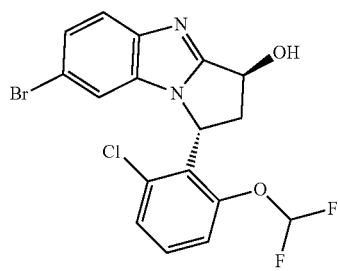 [SMILES: O[C@H]1C[C@H](c2c(Cl)cccc2OC(F)F)n2c1nc1ccc(Br)cc12]

(1R,3S)-7-Bromo-1-[2-chloro-6-(difluoromethoxy)phenyl]-2,3-dihydro-1H-pyrrolo[1,2-a]benzimidazol-3-ol—Alternative Procedure Intermediate 9 (3.63 g, 8.45 mmol) and triphenylphosphine (2.66 g, 10.14 mmol) were solubilized in anhydrous THF (34 mL), under an inert atmosphere of nitrogen. Acetic acid (0.5 mL, 9.30 mmol) was added and the mixture was cooled to 0° C. A solution of DIAD (2.62 mL, 12.62 mmol) in anhydrous THF (5 mL) was added dropwise. The reaction mixture was slowly warmed to r.t. and maintained for 2 h at r.t. The reaction mixture was diluted with EtOAc and washed with saturated aqueous $NaHCO_3$ solution. The organic layer was dried over anhydrous magnesium sulfate, then filtered and concentrated under vacuum. The resulting material (3.6 g) was solubilized in MeOH (40 mL). Potassium carbonate (1.1 g, 8.48 mmol) was added and the reaction mixture was stirred for 1 h at r.t. The solvent was evaporated, then the residue was taken up in EtOAc (50 mL) and water (20 mL). The organic layer was washed with water (2×20 mL) and dried over anhydrous sodium sulfate, then filtered and concentrated under vacuum, to give the title compound (4.9 g, crude) as a brown oil, which was utilised without further purification. LCMS basic (ES$^+$) 429/431/433 (M+H)$^+$, RT 2.46 minutes.

Preparative Intermediate 11

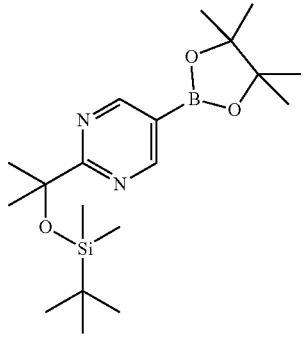 [SMILES: CC(C)(O[Si](C)(C)C(C)(C)C)c1ncc(B2OC(C)(C)C(C)(C)O2)cn1]

tert-Butyl(dimethyl){1-methyl-1-[5-(4,4,5,5-tetramethyl-1,3,2-dioxaborolan-2-yl)-pyrimidin-2-yl]ethoxy}silane 2-(1-Hydroxy-1-methylethyl)pyrimidine-5-boronic acid pinacol ester (10 g, 37.9 mmol), tert-butyldimethylchlorosilane (11.76 g, 75.7 mmol) and imidazole (7.89 g, 115.9 mmol) were dissolved in anhydrous DMF (150 mL). The reaction mixture was stirred at 85° C. for 4 days. EtOAc (100 mL) and water (250 mL) were added, then the aqueous layer was extracted with EtOAc (3×50 mL). The combined organic layers were washed with brine (3×20 mL) and dried over anhydrous magnesium sulfate, then filtered and concentrated in vacuo. The residue was purified by chromatography ($SiO_2$, 0-100% EtOAc in heptane) to afford the title compound (12.0 g, 84%) as a transparent oil. $\delta_H$ (400 MHz, $CDCl_3$) 9.04 (s, 2H), 1.70 (s, 6H), 1.40 (s, 12H), 0.94 (s, 9H), 0.01 (s, 6H).

Preparative Intermediate 12

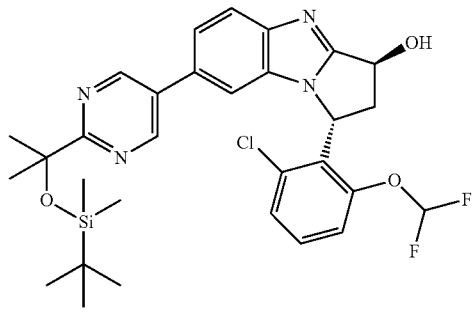 [SMILES: CC(C)(O[Si](C)(C)C(C)(C)C)c1ncc(-c2ccc3nc4n(c3c2)[C@@H](c2c(Cl)cccc2OC(F)F)C[C@@H]4O)cn1]

(1R,3S)-7-(2-{1-[tert-Butyl(dimethyl)silyl]oxy-1-methylethyl}pyrimidin-5-yl)-1-[2-chloro-6-(difluoromethoxy)phenyl]-2,3-dihydro-1H-pyrrolo[1,2-a]benzimidazol-3-ol Intermediate 10 (4.46 g, 10.4 mmol), Intermediate 11 (3.92 g, 10.4 mmol) and cesium carbonate (5.07 g, 15.6 mmol) were placed in a tube, which was filled with argon. Degassed 1,4-dioxane (37 mL) and degassed water (3.7 mL) were added and the resulting slurry was stirred at r.t. for 5 minutes before the addition of [1,1'-bis(diphenylphosphino)-ferrocene]dichloropalladium(II) (380 mg, 0.52 mmol). The reaction mixture was placed on a pre-heated stirring plate at 90° C. and stirred at this temperature for 2 h. The reaction mixture was cooled to r.t. before the addition of EtOAc (50 mL) and water (50 mL). The aqueous layer was extracted with EtOAc (3×20 mL), then the combined organic layers were dried over anhydrous magnesium sulfate, filtered and concentrated under reduced pressure. The crude residue was purified by chromatography (SiO$_2$, 30-100% EtOAc in hexane) to yield the title compound (5.7 g, 92%). LCMS acidic (ES+) 601.3/603.2 (M+H)$^+$, RT 3.64 minutes.

Preparative Intermediate 13

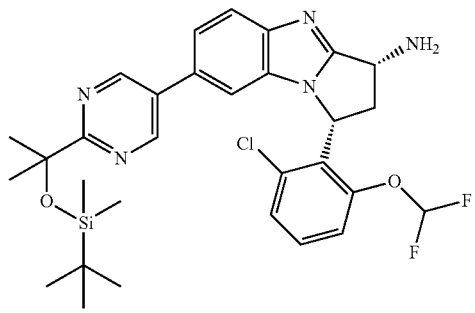 [SMILES: CC(C)(O[Si](C)(C)C(C)(C)C)c1ncc(-c2ccc3nc4n(c3c2)[C@@H](c2c(Cl)cccc2OC(F)F)C[C@H]4N)cn1]

(1R,3R)-7-(2-{1-[tert-Butyl(dimethyl)silyl]oxy-1-methylethyl}pyrimidin-5-yl)-1-[2-chloro-6-(difluoromethoxy)phenyl]-2,3-dihydro-1H-pyrrolo[1,2-a]benzimidazol-3-amine Intermediate 12 (11.18 g, 18.63 mmol) was suspended in dry toluene (34 mL). Diphenylphosphoryl azide (5.0 mL, 24.22 mmol) was added at 0° C., followed by the addition of 1,8-diazabicyclo[5.4.0]undec-7-ene (3.62 mL, 24.22 mmol). The reaction mixture was allowed to reach r.t. and stirred at r.t. for 2 h, then heated at 50° C. for 18 h. The reaction mixture was diluted with water (100 mL) and EtOAc (100 mL). The aqueous layer was extracted with EtOAc (3×100 mL). The combined organic layers were washed with saturated aqueous NH$_4$Cl solution and saturated aqueous NaHCO$_3$ solution, then dried over anhydrous magnesium sulfate, filtered and concentrated under vacuum. The crude residue was dissolved in a mixture of THF (172 mL) and water (17 mL) before the addition of a solution of trimethylphosphine in toluene (1 M, 34.6 mL, 20.8 mmol). The reaction mixture was stirred at r.t. for 2 h. The solvents were evaporated and the residue was purified by chromatography (SiO$_2$, 0-5% MeOH in DCM, 1% NH$_3$) to afford the title compound (7.0 g, 61%). LCMS basic (ES+) 600.3/602.3 (M+H)$^+$, RT 3.49 minutes.

Intermediate 14

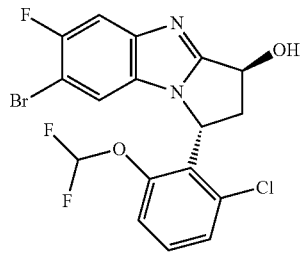 [SMILES: O[C@H]1C[C@H](c2c(Cl)cccc2OC(F)F)n2c1nc1cc(F)c(Br)cc12]

(1R,3S)-7-bromo-1-[2-chloro-6-(difluoromethoxy)phenyl]-6-fluoro-2,3-dihydro-1H-pyrrolo[1,2-a]benzimidazol-3-ol The title compound can be prepared from Intermediate 4 and 4-bromo-2,5-difluoronitrobenzene following the experimental procedure described for Intermediates 5 to 10.

Intermediate 15

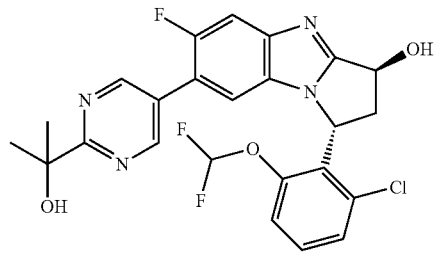 [SMILES: CC(C)(O)c1ncc(-c2cc3c(cc2F)nc2n3[C@@H](c3c(Cl)cccc3OC(F)F)C[C@@H]2O)cn1]

(1R,3S)-1-[2-Chloro-6-(difluoromethoxy)phenyl]-6-fluoro-7-[2-(2-hydroxypropan-2-yl-pyrimidin-5-yl]-2,3-dihydro-1H-pyrrolo[12-a]benzimidazol-3-ol The title compound can be prepared from Intermediate 14 and 2-[5-(4,4,5,5-tetramethyl-1,3,2-dioxaborolan-2-yl)pyrimidin-2-yl]propan-2-ol following the experimental procedure described for Intermediate 12.

Intermediate 16

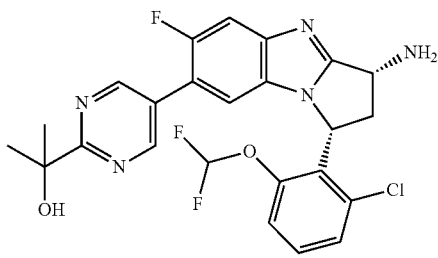 [SMILES: CC(C)(O)c1ncc(-c2cc3c(cc2F)nc2n3[C@@H](c3c(Cl)cccc3OC(F)F)C[C@H]2N)cn1]

2-(5-{(1R,3R)-3-Amino-1-[2-chloro-6-(difluoromethoxy)phenyl]-6-fluoro-2,3-dihydro-1H-pyrrolo[1,2-a]benzimidazol-7-yl}pyrimidin-2-yl)propan-2-ol The title compound can be prepared from Intermediate 15 following the experimental procedure described for Intermediate 13.

Intermediate 17

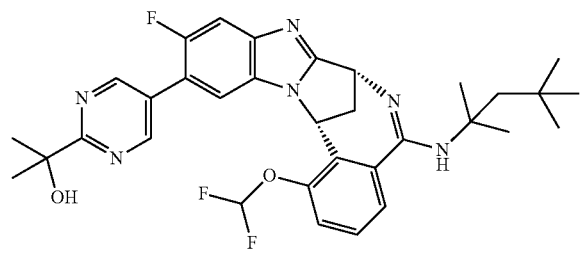 [SMILES: CC(C)(C)CC(C)(C)NC1=N[C@@H]2C[C@H](c3c(OC(F)F)cccc31)n1c2nc2cc(F)c(-c3cnc(C(C)(C)O)nc3)cc21]

(7R,14R)-1-(Difluoromethoxy)-10-fluoro-11-[2-(2-hydroxypropan-2-yl)pyrimidin-5-yl]-N-(2,4,4-trimethylpentan-2-yl)-7,14-dihydro-7,14-methanobenzimidazo[1,2-b]-[2,5]benzodiazocin-5-amine Intermediate 16 (1.82 mmol), cesium carbonate (772 mg, 2.37 mmol), 1,1'-bis-(diphenylphosphino)ferrocene (102 mg, 0.18 mmol), palladium(II) acetate (20.47 mg, 0.091 mmol) and 1,1,3,3-tetramethylbutyl isocyanide (518 μL, 2.73 mmol) were suspended in toluene (10 mL; dry and degassed with argon). The slurry was heated overnight at 110° C. under an atmosphere of argon. The reaction mixture was cooled to r.t., then diluted with EtOAc (10 mL) and water (5 mL). The two phases were separated and the aqueous layer was further extracted with EtOAc (2×10 mL). The combined organic layers were dried over anhydrous magnesium sulphate, then filtered and concentrated under reduced pressure. The crude material was purified by preparative HPLC (basic condition) to afford the title compound (442 mg, 40%). LCMS basic (ES+) 607 (M+H)+, RT 3.04 minutes.

Alternative Procedure 2-(5-{(1R,3R)-3-Amino-1-[2-bromo-6-(difluoromethoxy)phenyl]-6-fluoro-2,3-dihydro-1H-benzo[d]pyrrolo[1,2-a]imidazol-7-yl}pyrimidin-2-yl)propan-2-ol (WO 2016/050975, Intermediate 92) (1 g, 1.82 mmol), cesium carbonate (772 mg, 2.37 mmol), 1,1'-bis(diphenylphosphino)ferrocene (102 mg, 0.18 mmol), palladium(II) acetate (20.5 mg, 0.091 mmol) and 1,1,3,3-tetramethylbutyl isocyanide (518 μL, 2.73 mmol) were suspended in toluene (10 mL; dry and degassed with argon). The slurry was heated overnight at 110° C. under an atmosphere of argon. The reaction mixture was cooled to r.t., then diluted with EtOAc (10 mL) and water (5 mL). The two phases were separated and the aqueous phase was further extracted with EtOAc (2×10 mL). The combined organic phases were dried (MgSO4), filtered and concentrated in vacuo. The crude material was purified by preparative HPLC (basic, Method 2) to afford the title compound (442 mg, 40%). LCMS basic (ES+) 607 (M+H)+, RT 3.04 minutes (Method 1).

Intermediate 18

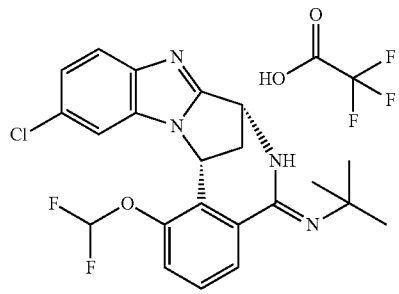

(7R,14R)—N-tert-Butyl-11-chloro-1-(difluoromethoxy)-6,7-dihydro-7,14-methanobenzimidazo[1,2-b][2.5]benzodiazocin-5(14H)-imine trifluoroacetate (1:1)

A mixture of (1R,3R)-1-[2-bromo-6-(difluoromethoxy)phenyl]-7-chloro-2,3-dihydro-1H-pyrrolo[1,2-a]benzimidazol-3-amine (WO 2016/050975 Intermediate 40) (0.25 g, 0.58 mmol), cesium carbonate (0.25 g, 0.76 mmol), 1,1'-bis(diphenylphosphino)-ferrocene (0.032 g, 0.058 mmol) and palladium(II) acetate (0.0065 g, 0.029 mmol) was degassed under 3 cycles of vacuum and argon. To the mixture were added tert-butyl isocyanide (0.073 g, 0.87 mmol) and degassed toluene (1.46 mL). The reaction mixture was stirred at 110° C. overnight. To the mixture were added water and EtOAc. The aqueous phase was extracted three times with EtOAc, then the organic phases were combined and washed sequentially with aqueous ammonium chloride solution and saturated aqueous sodium hydrogen carbonate solution. The organic phase was separated and dried (MgSO4), then filtered and concentrated in vacuo. The crude residue was purified by preparative HPLC (acidic, Method 1). The resulting material was partitioned between water and DCM. The aqueous phase was extracted with DCM, then the organic phases were combined and concentrated in vacuo, to afford the title compound (159 mg, 63%) as a yellow oil. $\delta_H$ (400 MHz, CDCl3) 9.22 (s, 1H), 8.95 (d, J 6.2 Hz, 1H), 8.09 (d, J 7.6 Hz, 1H), 7.94 (d, J 8.9 Hz, 1H), 7.74 (s, 1H), 7.70-7.57 (m, 2H), 7.53 (d, J 9.0 Hz, 1H), 6.99 (t, J 72.0 Hz, 1H), 6.81-6.74 (m, 1H), 6.69 (d, J 6.1 Hz, 1H), 4.12-3.90 (m, 1H), 3.21 (d, J 13.6 Hz, 1H), 1.73 (s, 9H).

Intermediate 19

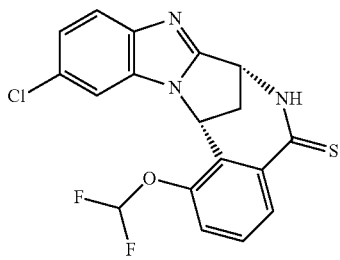 [SMILES: FC(F)Oc1cccc2c1[C@H]1C[C@@H](NC2=S)c2nc3ccc(Cl)cc3n21]

(7R,14R)-11-Chloro-1-(difluoromethoxy)-6,7-dihydro-7,14-methanobenzimidazo[1,2-b]-[2,5]benzodiazocin-5(14H-thione To a suspension of (7R,14R)-11-chloro-1-(difluoromethoxy)-6,7-dihydro-7,14-methanobenzimidazo[1,2-b][2,5]benzodiazocin-5(14H)-one (WO 2016/050975, Example 11) (1 g, 2.66 mmol) in toluene (50 mL) was added Lawesson's reagent (1.2 g, 2.9 mmol). The slurry was stirred overnight at 110° C. The reaction mixture was evaporated and diluted in a minimum amount of EtOAc. The precipitate was filtered and rinsed with diethyl ether (2×10 mL), then the filtrate was concentrated in vacuo, to afford the title compound (1.0 g, 96%) as a yellow solid. $\delta_H$ (400 MHz, DMSO-$d_6$) 11.56 (d, J 6.7 Hz, 1H), 9.05 (dd, J 8.3, 1.3 Hz, 1H), 7.79-7.40 (m, 5H), 7.23 (dd, J 8.7, 2.1 Hz, 1H), 6.36 (d, J 7.0 Hz, 1H), 5.12 (t, J 6.5 Hz, 1H), 3.55-3.38 (m, 1H), 2.77 (d, J 13.5 Hz, 1H). LCMS (ES+) 392 (M+H)+, RT 2.48 minutes (Method 2).

Intermediate 20

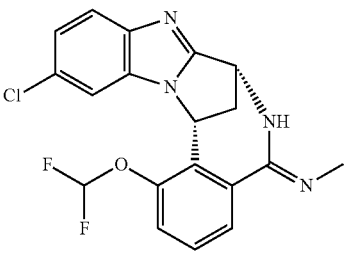 [SMILES: C/N=C1\N[C@@H]2C[C@H](c3c(OC(F)F)cccc31)n1c2nc2ccc(Cl)cc21]

(5Z,7R,14R)-11-Chloro-1-(difluoromethoxy)-N-methyl-6,7-dihydro-7,14-methanobenzimidazo[1,2-b][2,5]benzodiazocin-5(14H)-imine A mixture of Intermediate 19 (80.0 mg, 0.204 mmol) and 2M methylamine in THF (1.84 g, 4.08 mmol) was heated at 90° C. for 3 h in a microwave vial. Additional 2M methylamine in THF (0.5 mL) was added and the reaction mixture was heated at 90° C. for 4 h. The mixture was partitioned between water and EtOAc, then the organic phase was separated. The aqueous phase washed twice with EtOAc. The combined organic phases were dried and concentrated in vacuo. The resulting orange oil was purified by reverse-phase chromatography (pH 3) to afford the title compound (35 mg, 44%). LCMS (ES+) 389.0 (M+H)+, RT 1.24 minutes (Method 3).

Example 1

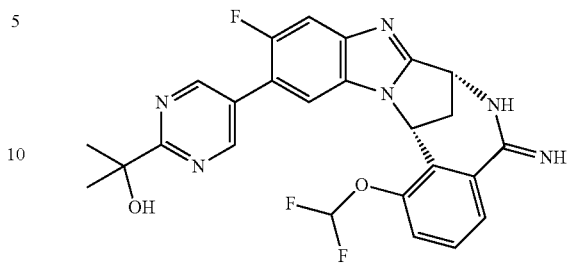

(7R,14R)-1-(Difluoromethoxy)-10-fluoro-5-imino-11-[2-(2-hydroxypropan-2-yl)-pyrimidin-5-yl]-7,14-dihydro-7,14-methanobenzimidazo[1,2-b][2,5]benzodiazocine Intermediate 17 (20 mg, 0.033 mmol) was suspended in 4N HCl in 1,4-dioxane (0.7 mL). TFA was added until the starting material dissolved. The reaction mixture was stirred at 100° C. for 2 h, then cooled to r.t. and diluted with EtOAc (2 mL) and saturated aqueous NaHCO$_3$ solution (2 mL). The two layers were separated and the aqueous layer was further extracted with EtOAc (2×2 mL). The combined organic layers were dried over anhydrous magnesium sulphate, then filtered and concentrated under reduced pressure. The crude material was purified by preparative LCMS (basic, Method 2) to afford the title compound (15 mg, 92%). $\delta_H$ (400 MHz, CDCl$_3$) 8.89 (m, 2H), 7.76 (d, J 7.4 Hz, 1H), 7.54 (m, 1H), 7.42 (m, 2H), 7.32 (m, 1H), 6.81 (m, 1H), 6.24 (d, J 7.2 Hz, 1H), 5.22 (m, 1H), 4.68 (m, 1H), 3.35 (m, 1H), 2.74 (m, 1H), 1.66 (s, 6H). LCMS (ES+) 495 (M+H)+, RT 1.94 minutes (Method 1). LCMS (ES+) 495 (M+H)+, RT 1.87 minutes (Method 2).

Example 2

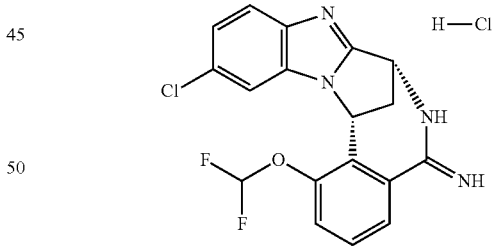

(7R,14R)-11-Chloro-1-(difluoromethoxy)-6,7-dihydro-7,14-methanobenzimidazo[1,2-b]-[2,5]benzodiazocin-5(14H)-imine hydrochloride Intermediate 18 (0.05 g, 0.092 mmol) was dissolved in 4N hydrochloric acid in 1,4-dioxane (0.23 mL, 1.160 mmol) and the reaction mixture was heated at 100° C. overnight. The precipitate was filtered, then washed with cold diisopropyl ether, to afford the title compound (20 mg, 58%). $\delta_H$ (400 MHz, DMSO-$d_6$) 11.21-11.00 (m, 1H), 9.59 (d, J 81.3 Hz, 2H), 8.05 (d, J 8.2 Hz, 1H), 7.89-7.40 (m, 5H), 7.26 (d, J 8.7 Hz, 1H), 6.41 (d, J 6.9 Hz, 1H), 5.41 (t, J 6.3 Hz, 1H), 4.10-3.94 (m, 1H), 2.95 (d, J 13.7 Hz, 1H). LCMS 375.09 (M+H)⁺, RT 2.18 minutes (Method 1). LCMS 375.1 (M+H)⁺, RT 1.94 minutes (Method 2).

Example 3

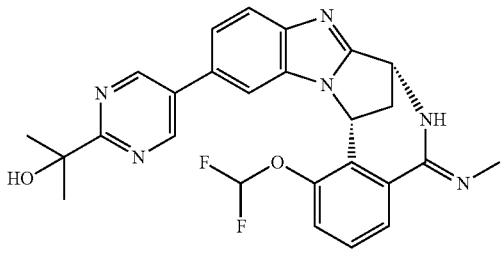 [SMILES: C/N=C1\N[C@@H]2C[C@H](c3c(OC(F)F)cccc31)n1c2nc2ccc(-c3cnc(C(C)(C)O)nc3)cc21]

2-{5-[(5Z,7R,14R)-1-(Difluoromethoxy)-5-(methylimino)-5,6,7,14-tetrahydro-7,14-methanobenzimidazo[1,2-b][2,5]benzodiazocin-11-yl]pyrimidin-2-yl}propan-2-ol Intermediate 20 (35 mg, 0.0900 mmol) was dissolved in 1,4-dioxane (0.90 mL) and was added to 2-(1-hydroxy-1-methylethyl)pyrimidine-5-boronic acid pinacol ester (48 mg, 0.180 mmol) and [1,1'-bis(diphenylphosphino)ferrocene]dichloropalladium(II) complex with dichloromethane (18.4 mg, 0.0225 mmol). Aqueous sodium carbonate solution (2M, 0.12 mL, 0.24 mmol) was added. The reaction mixture was degassed, then heated under microwave irradiation at 110° C. for 2 h. XPhos Pd G1 (16.6 mg, 0.0225 mmol) and 2-(1-hydroxy-1-methylethyl)pyrimidine-5-boronic acid pinacol ester (48 mg, 0.180 mmol) were added. The reaction mixture was degassed again and heated at 110° C. for a further 2 h. The reaction mixture was partitioned between EtOAc and water, then filtered through Celite. The organic phase was separated and the aqueous layer was washed twice with EtOAc. The combined organic phases were washed with brine, then dried and concentrated in vacuo. The resulting black oil was purified by reverse-phase HPLC (Method 3) to afford the title compound (16 mg, 36%). δ$_H$ (300 MHz, DMSO-d$_6$) 9.04 (s, 2H), 8.23 (s, 1H), 7.95-7.85 (m, 1H), 7.76-7.61 (m, 2H), 7.56 (dd, J 8.4, 1.8 Hz, 1H), 7.49-7.34 (m, 2H), 6.28 (d, J 7.0 Hz, 1H), 5.24 (d, J 5.6 Hz, 1H), 3.45-3.30 (m, 1H), 2.73 (s, 3H), 2.55 (d, J 12.8 Hz, 1H), 1.54 (s, 6H). LCMS (ES+) 491.0 (M+H)⁺, RT 1.61 minutes (Method 5). LCMS (ES+) 491.2 (M+H)⁺, RT 1.26 minutes (Method 6).

The invention claimed is:
1. A compound of formula (I) or an N-oxide thereof, or a pharmaceutically acceptable salt thereof:

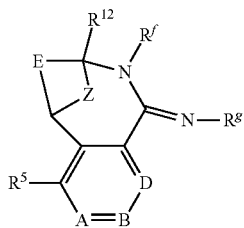

(I)

wherein
A represents N or C—R⁶;
B represents N or C—R⁷;
D represents N or C—R⁸;
Z represents methylene;
E represents a fused heteroaromatic ring system selected from the groups of formula (Ea), (Eb) and (Ec):

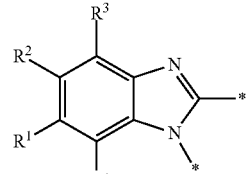

(Ea)

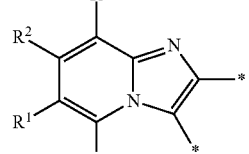

(Eb)

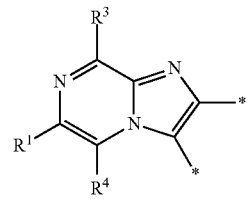

(Ec)

wherein the asterisks (*) represent the site of attachment of E to the remainder of the molecule;
R¹ represents hydrogen, halogen, cyano, trifluoromethyl, trifluoromethoxy, —ORᵃ, —SRᵃ, —SORᵃ, —SO₂Rᵃ, —NRᵇRᶜ, —NRᶜCORᵈ, —NRᶜCO₂Rᵈ, —NHCONRᵇRᶜ, —NRᵇSO₂Rᵉ, —CORᵈ, —CO₂Rᵈ, —CONRᵇRᶜ, —SO₂NRᵇRᶜ, or —S(O)(N—Rᵇ)Rᵉ; or R¹ represents C$_{1-6}$ alkyl, C$_{3-7}$ cycloalkyl, C$_{4-7}$ cycloalkenyl, aryl, aryl(C$_{1-6}$)alkyl, C$_{3-7}$ heterocycloalkyl, C$_{3-7}$ heterocycloalkenyl, heteroaryl, heteroaryl(C$_{1-6}$)alkyl, (C$_{3-7}$)heterocycloalkyl(C$_{1-6}$)alkyl-aryl-, (C$_{3-7}$)heterocycloalkenyl-aryl-, (C$_{3-7}$)cycloalkyl-heteroaryl-, (C$_{3-7}$)cycloalkyl-(C$_{1-6}$)alkyl-heteroaryl-, (C$_{4-7}$)cycloalkenyl-heteroaryl-, (C$_{4-9}$)bicycloalkyl-heteroaryl-, (C$_{3-7}$)heterocycloalkyl-heteroaryl-, (C$_{3-7}$)heterocycloalkyl(C$_{1-6}$)alkyl-heteroaryl-, (C$_{3-7}$)heterocycloalkenyl-heteroaryl-, (C$_{4-9}$)heterobicycloalkyl-heteroaryl- or (C$_{4-9}$)spiroheterocycloalkyl-heteroaryl-, any of which groups may be optionally substituted by one, two or three substituents independently selected from halogen, halo(C$_{1-6}$)alkyl, cyano, cyano(C$_{1-6}$)alkyl, nitro(C$_{1-6}$) alkyl, C$_{1-6}$ alkyl, phosphate(C$_{1-6}$)alkyl, (C$_{1-6}$)alkyl-phosphate(C$_{1-6}$)alkyl, phosphate(C$_{1-6}$)alkoxy(C$_{1-6}$) alkyl, sulphate(C$_{1-6}$)alkyl, difluoromethyl, trifluoromethyl, trifluoroethyl, C$_{2-6}$ alkenyl, hydroxy, hydroxy(C$_{1-6}$)alkyl, C$_{1-6}$ alkoxy, (C$_{1-6}$)alkoxy(C$_{1-6}$)-alkyl, trifluoroethoxy, carboxy(C$_{3-7}$)cycloalkyloxy, C$_{1-6}$ alkylthio, C$_{1-6}$ alkylsulphonyl, (C$_{1-6}$)alkylsulphonyl(C$_{1-6}$)alkyl, oxo, amino, amino(C$_{1-6}$) alkyl, C$_{1-6}$ alkylamino, di(C$_{1-6}$)-alkylamino, di(C$_{1-6}$)alkylamino(C$_{1-6}$)alkyl, (C$_{1-6}$)alkoxy(C$_{1-6}$)alkylamino, N—[(C$_{1-6}$)alkyl]-N-[hydroxy(C$_{1-6}$)alkyl]amino, (C$_{2-6}$)alkylcarbonylamino(C$_{1-6}$)alkyl, (C$_{2-6}$)alkoxycarbonyl-amino(C$_{1-6}$) alkyl, C$_{1-6}$ alkylsulphinylamino, C$_{1-6}$ alkylsulphonylamino, N—[(C$_{1-6}$)alkyl]-N—[(C$_{1-6}$)alkylsulphonyl]amino, bis [(C$_{1-6}$)alkylsulphonyl]amino, (C$_{1-6}$)alkylsulphonylamino- ($C_{1-6}$)alkyl, N—[($C_{1-6}$)alkyl]-N-[carboxy($C_{1-6}$)alkyl]amino, carboxy($C_{3-7}$)cycloalkylamino, carboxy($C_{3-7}$)cycloalkyl($C_{1-6}$)alkylamino, imino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxy-carbonyl($C_{1-6}$)alkyl, morpholinyl($C_{1-6}$)alkoxycarbonyl, $C_{2-6}$ alkoxycarbonylmethylidenyl, aminocarbonyl, aminosulphonyl, ($C_{1-6}$)alkylsulphoximinyl and [($C_{1-6}$)alkyl][N—($C_{1-6}$)-alkyl]sulphoximinyl;

$R^2$ represents hydrogen, halogen, cyano, nitro, hydroxy, trifluoromethyl, trifluoromethoxy or —$OR^a$; or $R^2$ represents $C_{1-6}$ alkyl or heteroaryl, either of which groups may be optionally substituted by one, two or three substituents independently selected from hydroxy ($C_{1-6}$)alkyl and $C_{2-6}$ alkoxycarbonyl;

$R^3$ and $R^4$ independently represent hydrogen, halogen or trifluoromethyl; or $C_{1-6}$ alkyl;

$R^5$ represents hydrogen, halogen, hydroxy, cyano, trifluoromethyl, difluoromethoxy, trifluoromethoxy, —$OR^a$ or $C_{1-6}$ alkylsulphonyl; or $R^5$ represents $C_{1-6}$ alkyl;

$R^6$, $R^7$ and $R^8$ independently represent hydrogen, halogen, trifluoromethyl, $C_{1-6}$ alkyl or $C_{1-6}$ alkoxy;

$R^{12}$ represents hydrogen or $C_{1-6}$ alkyl;

$R^a$ represents $C_{1-6}$ alkyl, $C_{3-7}$ cycloalkyl, aryl, aryl($C_{1-6}$) alkyl, $C_{3-7}$ heterocycloalkyl, heteroaryl or heteroaryl ($C_{1-6}$)alkyl, any of which groups may be optionally substituted by one or more substituents selected from $C_{1-6}$ alkoxy and oxo;

$R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl ($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents selected from $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, 6)alkylamino and $C_{2-6}$ alkoxycarbonylamino;

$R^c$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl ($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents selected from $C_{2-6}$ alkylcarbonyl and $C_{2-6}$ alkoxycarbonyl; or $R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl and (dioxo)-thiazinan-4-yl, any of which groups may be optionally substituted by one or more substituents selected from $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonyl-amino, $C_{2-6}$ alkylcarbonylamino($C_{1-6}$) alkyl, $C_{2-6}$ alkoxycarbonylamino, $C_{1-6}$ alkyl-sulphonylamino and aminocarbonyl;

$R^d$ represents hydrogen; or $R^d$ represents $C_{1-6}$ alkyl, $C_{3-7}$ cycloalkyl, aryl, $C_{3-7}$ heterocycloalkyl or heteroaryl, any of which groups may be optionally substituted by one or more substituents selected from halogen, $C_{1-6}$ alkyl, $C_{1-6}$ alkoxy, oxo, $C_{2-6}$ alkylcarbonyloxy and di($C_{1-6}$)alkylamino;

$R^e$ represents $C_{1-6}$ alkyl, aryl or heteroaryl, any of which groups may be optionally substituted by $C_{1-6}$ alkyl; and $R^f$ and $R^g$ independently represent hydrogen or $C_{1-6}$ alkyl.

2. The compound as claimed in claim 1 wherein A represents C—$R^6$, B represents C—$R^7$, and D represents C—$R^8$.

3. The compound as claimed in claim 1 represented by formula (IIA) or an N-oxide thereof, or a pharmaceutically acceptable salt thereof:

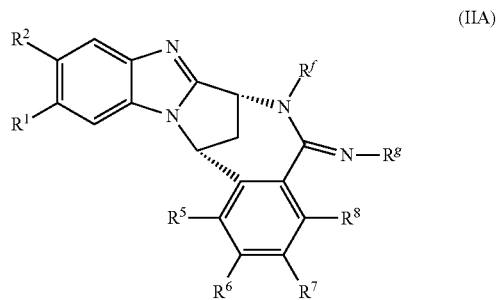

(IIA)

wherein $R^1$, $R^2$, $R^5$, $R^6$, $R^7$, $R^8$, $R^f$ and $R^g$ are as defined in claim 1.

4. The compound as claimed in claim 3 represented by formula (IIA-1) or an N-oxide thereof, or a pharmaceutically acceptable salt thereof:

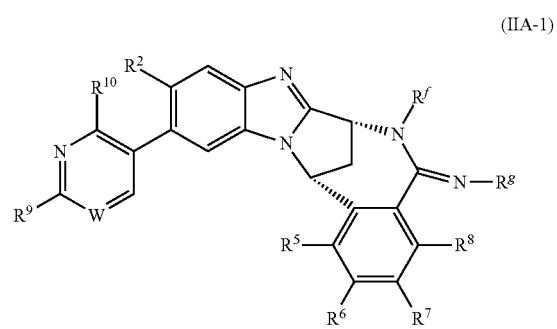

(IIA-1)

wherein
W represents N, CH or CF;
$R^9$ represents hydroxy($C_{1-6}$)alkyl or amino($C_{1-6}$)alkyl; and
$R^{10}$ represents hydrogen or $C_{1-6}$ alkyl.

5. The compound as claimed in claim 1 selected from the group consisting of
(7R,14R)-1-(Difluoromethoxy)-10-fluoro-5-imino-11-[2-(2-hydroxypropan-2-yl)-pyrimidin-5-yl]-7,14-dihydro-7,14-methanobenzimidazo[1,2-b][2,5]benzodiazocine;
(7R,14R)-11-Chloro-1-(difluoromethoxy)-6,7-dihydro-7,14-methanobenzimidazo[1,2-b]-[2,5]benzodiazocin-5(14H)-imine hydrochloride; and
2-{5-[(5Z,7R,14R)-1-(Difluoromethoxy)-5-(methylimino)-5,6,7,14-tetrahydro-7,14-methanobenzimidazo[1,2-b][2,5]benzodiazocin-11-yl]pyrimidin-2-yl}propan-2-ol.

6. A pharmaceutical composition comprising a compound of formula (I) as defined in claim 1 or an N-oxide thereof, or a pharmaceutically acceptable salt thereof, in association with a pharmaceutically acceptable carrier.

7. The pharmaceutical composition as claimed in claim 6 further comprising an additional pharmaceutically active ingredient.

8. A method for the treatment of an inflammatory or autoimmune disorder, wherein the inflammatory or autoimmune disorder is rheumatoid arthritis or Crohn's disease, which comprises administering to a patient in need of such treatment an effective amount of a compound of formula (I) as defined in claim 1 or an N-oxide thereof, or a pharmaceutically acceptable salt thereof.

9. The compound as claimed in claim 2 wherein:
- $R^1$ represents halogen; or $R^1$ represents heteroaryl, which group may be optionally substituted by one, two or three substituents independently selected from halogen, cyano, $C_{1-6}$ alkyl, difluoromethyl, hydroxy($C_{1-6}$)alkyl, oxo, amino and amino($C_1$-6)alkyl;
- $R^2$ represents hydrogen or halogen;
- $R^3$ represents hydrogen, halogen or $C_{1-6}$ alkyl;
- $R^4$ represents hydrogen, halogen or $C_{1-6}$ alkyl;
- $R^5$ represents difluoromethoxy or —$OR^a$;
- $R^6$ represents hydrogen, halogen or trifluoromethyl;
- $R^7$ represents hydrogen or trifluoromethyl;
- $R^8$ represents hydrogen or trifluoromethyl;
- $R^{12}$ represents hydrogen;
- $R^a$ represents $C_{1-6}$ alkyl, aryl($C_{1-6}$)alkyl or heteroaryl($C_{1-6}$)alkyl, any of which groups may be optionally substituted by one or more substituents selected from $C_{1-6}$ alkoxy and oxo;
- $R^f$ represents hydrogen or methyl; and
- $R^g$ represents hydrogen or methyl.

\* \* \* \* \*